(12) United States Patent
Madsen et al.

(10) Patent No.: US 11,628,260 B2
(45) Date of Patent: Apr. 18, 2023

(54) MULTIPLE DOSAGE INJECTOR WITH RACK AND PINION DOSAGE SYSTEM

(71) Applicant: ANTARES PHARMA, INC., Ewing, NJ (US)

(72) Inventors: Patrick Madsen, Litchfield, MN (US); Hans Pflaumer, Roseville, MN (US); Kevin Swanson, Plymouth, MN (US)

(73) Assignee: ANTARES PHARMA, INC., Ewing, NJ (US)

( * ) Notice: Subject to any disclaimer, the term of this patent is extended or adjusted under 35 U.S.C. 154(b) by 488 days.

(21) Appl. No.: 16/797,447

(22) Filed: Feb. 21, 2020

(65) Prior Publication Data

US 2020/0188603 A1     Jun. 18, 2020

Related U.S. Application Data

(63) Continuation of application No. 15/650,332, filed on Jul. 14, 2017, now Pat. No. 10,610,649, which is a continuation of application No. 14/204,641, filed on Mar. 11, 2014, now Pat. No. 9,707,354.

(60) Provisional application No. 61/776,269, filed on Mar. 11, 2013.

(51) Int. Cl.
*A61M 5/315* (2006.01)

(52) U.S. Cl.
CPC .... *A61M 5/31585* (2013.01); *A61M 5/31575* (2013.01); *A61M 5/31586* (2013.01); *A61M 5/31595* (2013.01)

(58) Field of Classification Search
CPC .......... A61M 5/31575; A61M 5/31585; A61M 5/31586; A61M 5/31595
See application file for complete search history.

(56) References Cited

U.S. PATENT DOCUMENTS

| | | | |
|---|---|---|---|
| 547,370 | A | 10/1895 | Chalefou |
| 1,465,793 | A | 8/1923 | Schilling |
| 1,512,294 | A | 10/1924 | Marcy |
| 1,687,323 | A | 10/1928 | Cook |
| 2,354,649 | A | 8/1944 | Bruckner |
| 2,607,344 | A | 8/1952 | Brown |

(Continued)

FOREIGN PATENT DOCUMENTS

| | | |
|---|---|---|
| AR | 00081651 | 10/2012 |
| AR | 082053 | 11/2012 |

(Continued)

OTHER PUBLICATIONS

"Skin", American Medical Association (AMA) Current Procedural Terminology , 1998, http://www.ama-assn.org/ama/pub/category/print/7176.html, 1 page.

(Continued)

*Primary Examiner* — Brandy S Lee
(74) *Attorney, Agent, or Firm* — Morgan, Lewis & Bockius LLP

(57) ABSTRACT

A dispensing mechanism for delivering a dosage of medicament including a housing, a push button, a crank arm that is slideably engageable with the push button, a ram, and a ratchet gear releasably engageable with the crank arm and ram, translation of the push button along an axis causing the crank arm to engage and rotate the ratchet gear which causes the ram to distally advance relative to the housing.

21 Claims, 30 Drawing Sheets

(56) References Cited

U.S. PATENT DOCUMENTS

| | | |
|---|---|---|
| 2,645,223 A | 7/1953 | Lawshe |
| 2,648,334 A | 8/1953 | Brown |
| 2,687,730 A | 8/1954 | Hein |
| 2,688,967 A | 9/1954 | Huber |
| 2,699,166 A | 1/1955 | Bickinson |
| 2,717,601 A | 9/1955 | Brown |
| 2,728,341 A | 12/1955 | Roehr |
| 2,737,946 A | 3/1956 | Hein, Jr. |
| 2,813,528 A | 11/1957 | Blackman |
| 2,866,458 A | 12/1958 | Mesa et al. |
| 2,888,924 A | 6/1959 | Dunmire |
| 2,893,390 A | 7/1959 | Lockhart |
| 3,130,724 A | 4/1964 | Higgins |
| 3,166,069 A | 1/1965 | Enstrom |
| 3,375,825 A | 4/1968 | Keller |
| 3,382,865 A | 5/1968 | Worrall |
| 3,526,225 A | 9/1970 | Hayamamachi |
| 3,557,784 A | 1/1971 | Shields |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | af Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |
| 5,163,907 A | 11/1992 | Szuszkiewicz |
| 5,176,643 A | 1/1993 | Kramer et al. |
| 5,180,370 A | 1/1993 | Gillespie |
| 5,185,985 A | 2/1993 | Vetter et al. |
| 5,195,983 A | 3/1993 | Boese |
| 5,221,348 A | 6/1993 | Masano |
| 5,226,895 A | 7/1993 | Harris |
| 5,232,459 A | 8/1993 | Hjertman |
| 5,256,142 A | 10/1993 | Colavecchio |
| 5,263,934 A | 11/1993 | Haak |
| 5,271,744 A | 12/1993 | Kramer et al. |
| 5,279,543 A | 1/1994 | Glikfeld et al. |
| 5,279,576 A | 1/1994 | Loo et al. |
| 5,279,585 A | 1/1994 | Balkwill |
| 5,279,586 A | 1/1994 | Balkwill |
| 5,281,198 A | 1/1994 | Haber et al. |
| 5,290,228 A | 3/1994 | Uemura et al. |
| 5,295,965 A | 3/1994 | Wilmot |
| 5,300,030 A | 4/1994 | Crossman et al. |
| 5,304,128 A | 4/1994 | Haber et al. |
| 5,304,152 A | 4/1994 | Sams |
| 5,308,341 A | 5/1994 | Chanoch |
| 5,318,522 A | 6/1994 | D'Antonio |
| 5,320,603 A | 6/1994 | Vetter et al. |
| 5,330,431 A | 7/1994 | Herskowitz |
| 5,332,399 A | 7/1994 | Grabenkort et al. |
| 5,334,144 A | 8/1994 | Alchas et al. |
| 5,342,308 A | 8/1994 | Boschetti |
| 5,350,367 A | 9/1994 | Stiehl et al. |
| 5,354,286 A | 10/1994 | Mesa et al. |
| 5,358,489 A | 10/1994 | Wyrick |
| RE34,845 E | 1/1995 | Vetter et al. |
| 5,391,151 A | 2/1995 | Wilmot |
| 5,405,362 A | 4/1995 | Kramer et al. |
| 5,415,648 A | 5/1995 | Malay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,505,694 A | 4/1996 | Hubbard et al. |
| 5,514,097 A | 5/1996 | Knauer |
| 5,514,107 A | 5/1996 | Haber et al. |
| 5,540,664 A | 7/1996 | Wyrick |
| 5,542,760 A | 8/1996 | Chanoch et al. |
| 5,544,234 A | 8/1996 | Terajima et al. |
| 5,549,561 A | 8/1996 | Hjertman |
| 5,554,134 A | 9/1996 | Bonnichsen |
| 5,562,625 A | 10/1996 | Stefancin, Jr. |
| 5,567,160 A | 10/1996 | Massino |
| 5,569,190 A | 10/1996 | D'Antonio |
| 5,569,192 A | 10/1996 | van der Wal |
| 5,569,236 A | 10/1996 | Kriesel |

(56) References Cited

U.S. PATENT DOCUMENTS

| | | |
|---|---|---|
| 5,573,042 A | 11/1996 | De Haen |
| 5,593,388 A | 1/1997 | Phillips |
| 5,599,302 A | 2/1997 | Lilley et al. |
| 5,599,309 A | 2/1997 | Marshall et al. |
| 5,605,542 A | 2/1997 | Tanaka et al. |
| 5,637,094 A | 6/1997 | Stewart, Jr. et al. |
| 5,637,100 A | 6/1997 | Sudo |
| 5,649,912 A | 7/1997 | Peterson |
| 5,658,259 A | 8/1997 | Pearson et al. |
| 5,665,071 A | 9/1997 | Wyrick |
| 5,688,251 A | 11/1997 | Chanoch |
| 5,695,472 A | 12/1997 | Wyrick |
| 5,704,911 A | 1/1998 | Parsons |
| 5,725,508 A | 3/1998 | Chanoch et al. |
| 5,730,723 A | 3/1998 | Castellano et al. |
| 5,743,889 A | 4/1998 | Sams |
| 5,769,138 A | 6/1998 | Sadowski et al. |
| 5,785,691 A | 7/1998 | Vetter et al. |
| 5,788,670 A | 8/1998 | Reinhard et al. |
| 5,801,057 A | 9/1998 | Smart et al. |
| 5,807,309 A | 9/1998 | Lundquist et al. |
| 5,820,602 A | 10/1998 | Kovelman et al. |
| 5,820,622 A | 10/1998 | Gross et al. |
| 5,827,232 A | 10/1998 | Chanoch et al. |
| 5,836,911 A | 11/1998 | Marzynski et al. |
| 5,843,036 A | 12/1998 | Olive et al. |
| 5,846,233 A | 12/1998 | Lilley et al. |
| 5,851,197 A | 12/1998 | Marano et al. |
| 5,851,198 A | 12/1998 | Castellano et al. |
| 5,860,456 A | 1/1999 | Bydlon et al. |
| 5,865,795 A | 2/1999 | Schiff et al. |
| 5,865,799 A | 2/1999 | Tanaka et al. |
| 5,868,711 A | 2/1999 | Kramer et al. |
| 5,873,857 A | 2/1999 | Kriesel |
| 5,875,976 A | 3/1999 | Nelson et al. |
| 5,879,327 A | 3/1999 | DeFarges et al. |
| 5,891,085 A | 4/1999 | Lilley et al. |
| 5,891,086 A | 4/1999 | Weston |
| 5,893,842 A | 4/1999 | Imbert |
| 5,919,159 A | 7/1999 | Lilley et al. |
| 5,921,966 A | 7/1999 | Bendek et al. |
| 5,925,017 A | 7/1999 | Kriesel et al. |
| 5,928,205 A | 7/1999 | Marshall |
| 5,935,949 A | 8/1999 | White |
| 5,951,528 A | 9/1999 | Parkin |
| 5,957,897 A | 9/1999 | Jeffrey |
| 5,960,797 A | 10/1999 | Kramer et al. |
| 5,989,227 A | 11/1999 | Vetter et al. |
| 6,004,297 A | 12/1999 | Steenfeldt-Jensen et al. |
| 6,045,534 A | 4/2000 | Jacobson et al. |
| 6,056,716 A | 5/2000 | D'Antonio et al. |
| 6,077,247 A | 6/2000 | Marshall et al. |
| 6,083,201 A | 7/2000 | Skinkle |
| 6,090,070 A | 7/2000 | Hager et al. |
| 6,099,504 A | 8/2000 | Gross et al. |
| 6,123,684 A | 9/2000 | Deboer et al. |
| 6,132,395 A | 10/2000 | Landau et al. |
| 6,159,181 A | 12/2000 | Crossman et al. |
| 6,171,276 B1 | 1/2001 | Lippe et al. |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,221,053 B1 | 4/2001 | Walters et al. |
| 6,223,408 B1 | 5/2001 | Vetter et al. |
| 6,231,540 B1 | 5/2001 | Smedegaard |
| 6,241,709 B1 | 6/2001 | Bechtold et al. |
| 6,245,347 B1 | 6/2001 | Zhang et al. |
| 6,258,078 B1 | 7/2001 | Thilly |
| 6,264,629 B1 | 7/2001 | Landau |
| 6,270,479 B1 | 8/2001 | Bergens et al. |
| 6,309,371 B1 | 10/2001 | Deboer et al. |
| 6,319,224 B1 | 11/2001 | Stout et al. |
| 6,371,939 B2 | 4/2002 | Bergens et al. |
| 6,383,168 B1 | 5/2002 | Landau et al. |
| 6,391,003 B1 | 5/2002 | Lesch, Jr. |
| 6,406,456 B1 | 6/2002 | Slate et al. |
| 6,428,528 B2 | 8/2002 | Sadowski et al. |
| 6,471,669 B2 | 10/2002 | Landau |
| 6,494,865 B1 | 12/2002 | Alchas |
| 6,517,517 B1 | 2/2003 | Farrugia et al. |
| 6,530,904 B1 | 3/2003 | Edwards et al. |
| 6,544,234 B1 | 4/2003 | Gabriel |
| 6,562,006 B1 | 5/2003 | Hjertman et al. |
| 6,565,553 B2 | 5/2003 | Sadowski et al. |
| 6,568,259 B2 | 5/2003 | Saheki et al. |
| 6,569,123 B2 | 5/2003 | Alchas et al. |
| 6,569,143 B2 | 5/2003 | Alchas et al. |
| 6,584,910 B1 | 7/2003 | Plass |
| 6,589,210 B1 | 7/2003 | Rolfe |
| 6,607,508 B2 | 8/2003 | Knauer |
| 6,620,137 B2 | 9/2003 | Kirchhofer et al. |
| 6,641,561 B1 | 11/2003 | Hill et al. |
| 6,645,170 B2 | 11/2003 | Landau |
| 6,656,150 B2 | 12/2003 | Hill et al. |
| 6,673,035 B1 | 1/2004 | Rice et al. |
| 6,682,504 B2 | 1/2004 | Nelson et al. |
| 6,689,092 B2 | 2/2004 | Zierenberg et al. |
| 6,706,000 B2 | 3/2004 | Perez et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,830,560 B1 | 12/2004 | Gross et al. |
| 6,899,698 B2 | 5/2005 | Sams |
| 6,932,793 B1 | 8/2005 | Marshall et al. |
| 6,932,794 B2 | 8/2005 | Giambattista et al. |
| 6,936,032 B1 | 8/2005 | Bush, Jr. et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,018,364 B2 | 3/2006 | Giambattista et al. |
| 7,066,907 B2 | 6/2006 | Crossman et al. |
| 7,112,187 B2 | 9/2006 | Karlsson |
| 7,118,552 B2 | 10/2006 | Shaw et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,220,247 B2 | 5/2007 | Shaw et al. |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,442,185 B2 | 10/2008 | Amark et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,500,964 B2 | 3/2009 | Shaw et al. |
| 7,517,334 B2 | 4/2009 | Jacobs et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |

(56) References Cited

U.S. PATENT DOCUMENTS

| | | | |
|---|---|---|---|
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 8,882,723 B2 * | 11/2014 | Smith ............... A61M 5/31555 604/211 |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Arnisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0220524 A1 | 11/2004 | Sadowski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0080377 A1 | 4/2005 | Sadowski et al. |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0069355 A1 | 3/2006 | Judson |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0088288 A1 | 4/2007 | Barron et al. |
| 2007/0093775 A1 | 4/2007 | Daly |
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |

(56) References Cited

U.S. PATENT DOCUMENTS

| | | |
|---|---|---|
| 2009/0204062 A1 | 8/2009 | Muto et al. |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch et al. |
| 2009/0304812 A1 | 12/2009 | Staniforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Cleathero |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |

(56) References Cited

U.S. PATENT DOCUMENTS

| | | |
|---|---|---|
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041241 A1* | 2/2013 | Felts ............ C23C 16/52 604/199 |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |

(56) References Cited

FOREIGN PATENT DOCUMENTS

| | | |
|---|---|---|
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1067823 | 1/2001 |
| EP | 1161961 | 12/2001 |
| EP | 1307012 | 5/2003 |
| EP | 1518575 | 3/2005 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |

(56) References Cited

FOREIGN PATENT DOCUMENTS

| | | |
|---|---|---|
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | WO 97/14455 | 4/1997 |
| WO | WO 97/21457 | 6/1997 |
| WO | WO 1997/41907 | 11/1997 |
| WO | WO 97/48430 | 12/1997 |
| WO | WO 1998/031369 | 7/1998 |
| WO | WO 1998/032451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | WO 1999/062525 | 12/1999 |
| WO | WO 9962525 | 12/1999 |
| WO | WO 0006228 | 2/2000 |
| WO | WO 00/24441 | 5/2000 |
| WO | WO 00/29050 | 5/2000 |
| WO | WO 01/93926 | 12/2001 |
| WO | WO 02/083216 | 10/2002 |
| WO | WO 2002/089805 | 11/2002 |
| WO | WO 2089805 | 11/2002 |
| WO | WO 3047663 | 6/2003 |
| WO | WO 2003/070296 | 8/2003 |
| WO | WO 3068290 | 8/2003 |
| WO | WO 03070296 | 8/2003 |
| WO | WO 2003/097133 | 11/2003 |
| WO | WO 3097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/086899 | 8/2006 |
| WO | WO 2006/125328 | 11/2006 |
| WO | WO 2006/130098 | 12/2006 |
| WO | WO 2007/047200 | 4/2007 |
| WO | WO 2007/063342 | 6/2007 |
| WO | WO 2007/100899 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |
| WO | WO 2008/107378 | 9/2008 |
| WO | WO 2008/112472 | 9/2008 |
| WO | WO 2007/104636 | 12/2008 |
| WO | WO 2009049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |

(56) References Cited

FOREIGN PATENT DOCUMENTS

| | | |
|---|---|---|
| WO | WO 2011/048223 | 4/2011 |
| WO | WO 2011/048422 | 4/2011 |
| WO | WO 2011/050359 | 4/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2011/051366 | 9/2012 |
| WO | WO 2012/122643 | 9/2012 |

OTHER PUBLICATIONS

Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.
Chen et al., "Blood Lipid Profiles and Peripheral Blood Mononuclear Cell Cholesterol Metabolism Gene Expression in Patients with and Without Methotrexate" BMC Medicine, 2011,9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31(6), pp. 361-366.
Hoekstra et al., Bioavailability of Higher Dose Methotrexate Comparing Oral and Subcutaneous Administration i n Patients with Rheumatoid Arthritis, The Journal of Rheumatology, 2004, 31(4), pp. 645-648.
International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.
"The Historical Development of Jet Injection and Envisioned Uses in Mass Immunization and Mass Therapy Based Upon Two Decades' Experience", Military Medicine, Jun. 1963, 128, pp. 516-524.
Pehling et al., "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in

(56) References Cited

OTHER PUBLICATIONS

Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US2013/029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Lunenfeld, "Stable Testosterone Levels Achieved with Subcutaneous Testosterone Injections", The aging Male, Mar. 2006, 9(1), 70 pages.
European Office Action for EP Application No. 19 173 290.8; dated Apr. 22, 2020; 5 pages.
Extended European Search Report dated Oct. 24, 2019 for European Patent Application No. 19173290.8, 6 pages.
International Patent Application No. PCT/US14/23883, International Search Report, dated Jul. 10, 2014, 3 pages.
International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
European Patent Office Communication Report Reference EP102555, for European Patent Application 14778806.1, dated Feb. 18, 2016, 6 pages.
European Search Report and Written Opinion dated Oct. 24, 2019 for European Patent Application No. 19173290, 6 pages.

\* cited by examiner

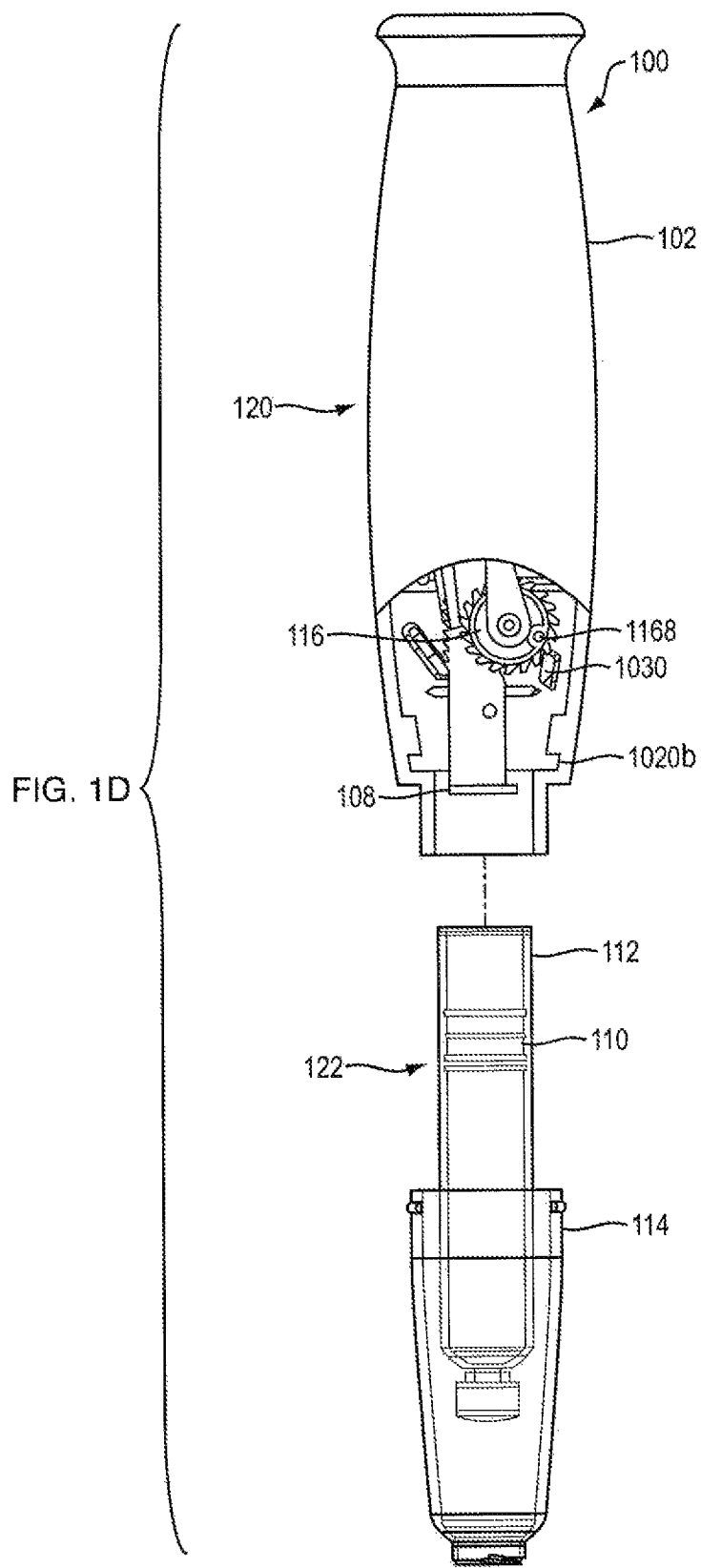

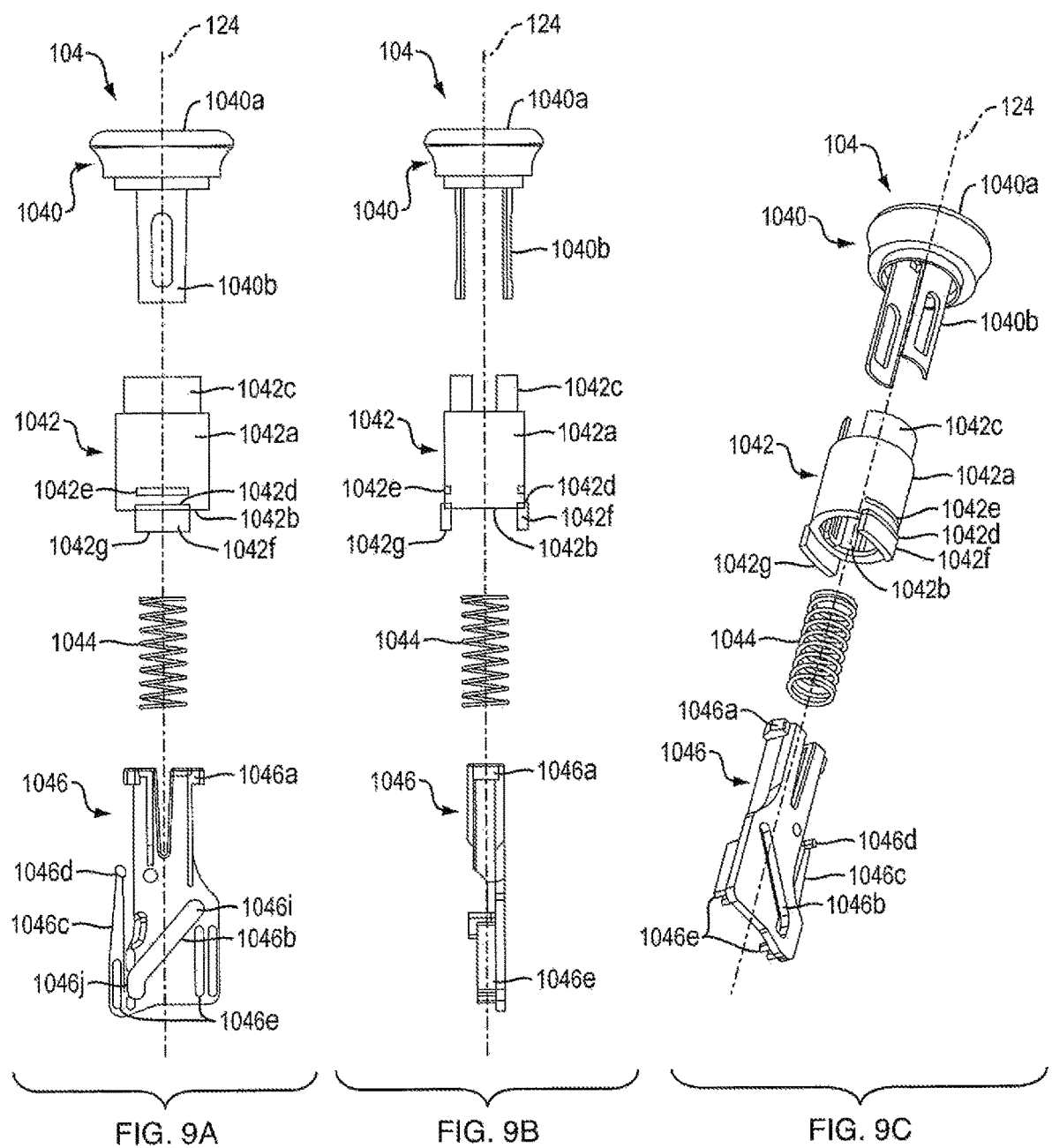

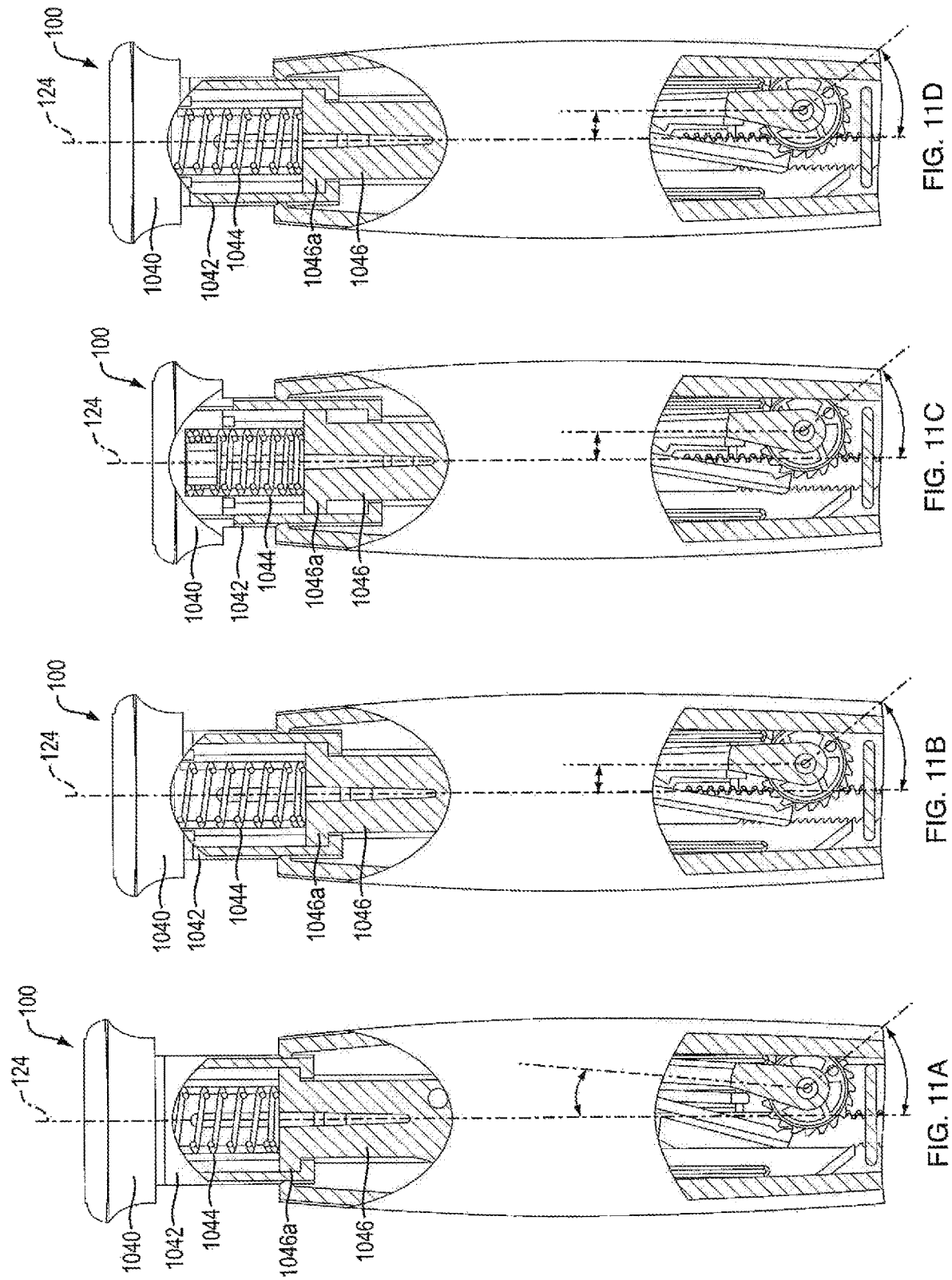

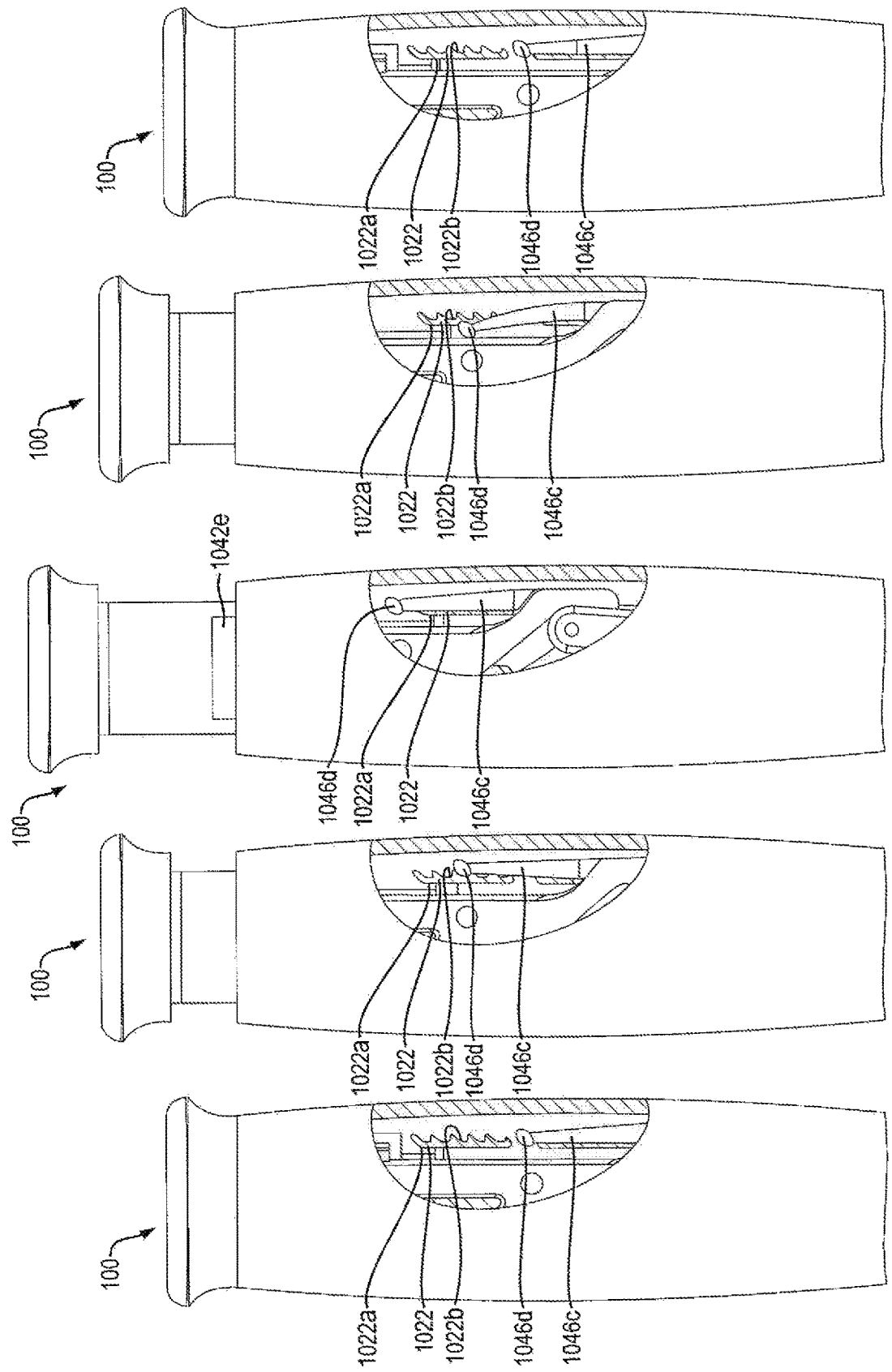

MULTIPLE DOSAGE INJECTOR WITH RACK AND PINION DOSAGE SYSTEM

CROSS REFERENCE TO RELATED APPLICATIONS

This application is a continuation of U.S. application Ser. No. 15/650,332 filed Jul. 14, 2017 which is a continuation of U.S. patent application Ser. No. 14/204,641 filed Mar. 11, 2014, now U.S. Pat. No. 9,707,354, which claims priority of U.S. Provisional Patent Application No. 61/776,269 filed Mar. 11, 2013, each of which is incorporated by reference herein for all purposes.

FIELD OF THE DISCLOSURE

The present invention relates to an injection device capable of delivering multiple doses of a liquid medicament contained therein without the need to refill the device between doses.

BACKGROUND

Various types of drug treatments, including hormone therapy and the like, require administration of the drug-containing liquid medicament at regular intervals over an extended period of time. For example, a specific hormone treatment can require daily administration of the drug for a period of thirty days. In such a situation, it is advantageous to provide a device that allows the patient to self-administer the injection to avoid repeated trips to a doctor's office or the like.

A device is needed that allows for repeated administration of a dose of medicament that is easy to use correctly in self-administration.

SUMMARY

In one embodiment, the present invention is a dispensing mechanism, including a housing having a proximal-distal axis; a ram within the housing and movable in a distal direction; a user-operable push button moveable along the proximal-distal axis relative to the housing, the push button including a slot at a distal portion of the push button; a crank arm having pawl tooth, a pivot point, and a crank arm protrusion slideably engageable with the slot such that movement of the push button causes the crank arm protrusion to move along the slot, causing rotation of the crank arm about the pivot point; and a ratchet gear having a first set of teeth releasably engageable with the pawl tooth and a second set of teeth releaseably engageable with the ram, wherein engagement of the pawl tooth with the first set of teeth of the ratchet gear causes the ratchet gear to rotate, causing the ram to distally advance relative to the housing.

In another embodiment, the dispensing mechanism further includes an anti-reverse mechanism including at least one housing ratchet integrally formed on an internal surface of the housing on both housing parts; and a flexible column integrally formed extending from a distal portion of the push button, the flexible column having a flexible column protrusion at a proximal end thereof, wherein as the push button moves along the proximal-distal axis, the flexible column protrusion slides between the integrally formed ratchets on both housing parts and engages the housing ratchets and restricts movement of the push button to one direction during a resetting motion. In another embodiment, the flexible column protrusion is almond shaped and thicker than said column. In one embodiment, having ratchets on both housing parts, the column sliding between them, and the almond engaging said ratchets allows the ratchet and column to be supported in a double shear type fashion further strengthening and balancing applied loads on said mechanism. In one embodiment, only one housing part contains an integrally formed ratchet, which makes the mechanism operate in single shear and tends to be unbalanced and weaker than other configurations.

In another embodiment, the ram includes at least two sets of teeth. In one embodiment, a first set of ram teeth are configured to engage the second set of teeth of the ratchet gear, and a second set of ram teeth are configured to engage a housing protrusion, the housing protrusion being integrally formed within the housing and configured to facilitate movement of the ram in one direction. In another embodiment, the second set of ratchet gear teeth are releasably engageable with a housing protrusion being integrally formed within the housing and configured to facilitate rotation of the gear in one direction.

In one embodiment, the push button slot is oriented at an oblique angle with respect to the proximal-distal axis.

In one embodiment, the push button slot has a portion that is oriented at an oblique angle with respect to the proximal-distal axis and a portion that has varying angles to the proximal-distal axis.

In one embodiment, the invention is an injector including the dispensing mechanism; a cartridge disposed within the housing; a plunger disposed in the cartridge to seal a medicament therein, wherein the ram is associated with the plunger for forcing the plunger in a distal direction for ejecting a dose of medicament; and a needle in fluid communication with the cartridge for injecting the doses into a patient. In one embodiment, the medicament is administered at a fixed dose repetitively. In one embodiment, the medicament is administered in varying doses. In one embodiment, the medicament includes a parathyroid hormone. In another embodiment, the hormone is teriparatide. In one embodiment, the medicament includes a glucagon-like peptide-1 agonist. In another embodiment, the glucagon-like peptide-1 agonist is exenatide.

BRIEF DESCRIPTION OF THE DRAWINGS

These and other objects, features and advantages of the invention will be apparent from a consideration of the following non-limiting detailed description considered in conjunction with the drawing figures, in which:

FIG. 1D is a side partial view of an injection device according to an exemplary embodiment of the present disclosure;

FIGS. 9A, 9B, and 9C are side exploded views of a second exemplary user-manipulable push button of the injection device shown in FIG. 1D;

FIGS. 11A, 11B, 11C, and 11D are a partial side cutaway views of the injection device shown in FIG. 1D showing compression of an exemplary force limiting biasing member;

FIGS. 12A, 12B, 12C, 12D, and 12E are partial side cutaway views of an anti-reverse feature of the injection device shown in FIG. 1D;

Figure 1A:
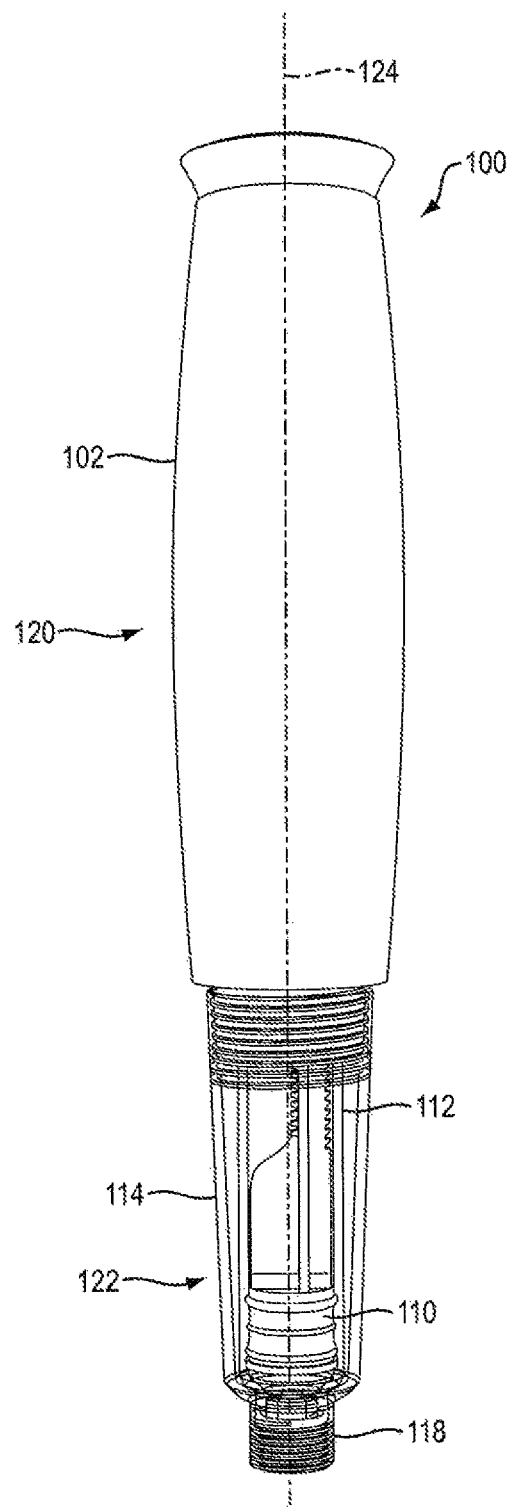
FIG. 1A is a side view of an injection device according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

Referring to the drawings in detail, wherein like reference numerals indicate like elements throughout, there is shown in FIGS. 1-21 an injection device 100, in accordance with an exemplary embodiment of the present invention. It is noted that, in the context of this disclosure, the terms "distal" and "proximal" are used in reference to the position of injection device 100 relative to a user of the injection device when merely held by a user. Accordingly, a point located distal to a second point would be further from the user (e.g., towards an injection end of injection device 100) and vice versa.

FIGS. 1A-1C and 2-8 show one embodiment of the present invention and FIGS. 1D and 9-21 show another embodiment of the present invention.

Figure 14A:
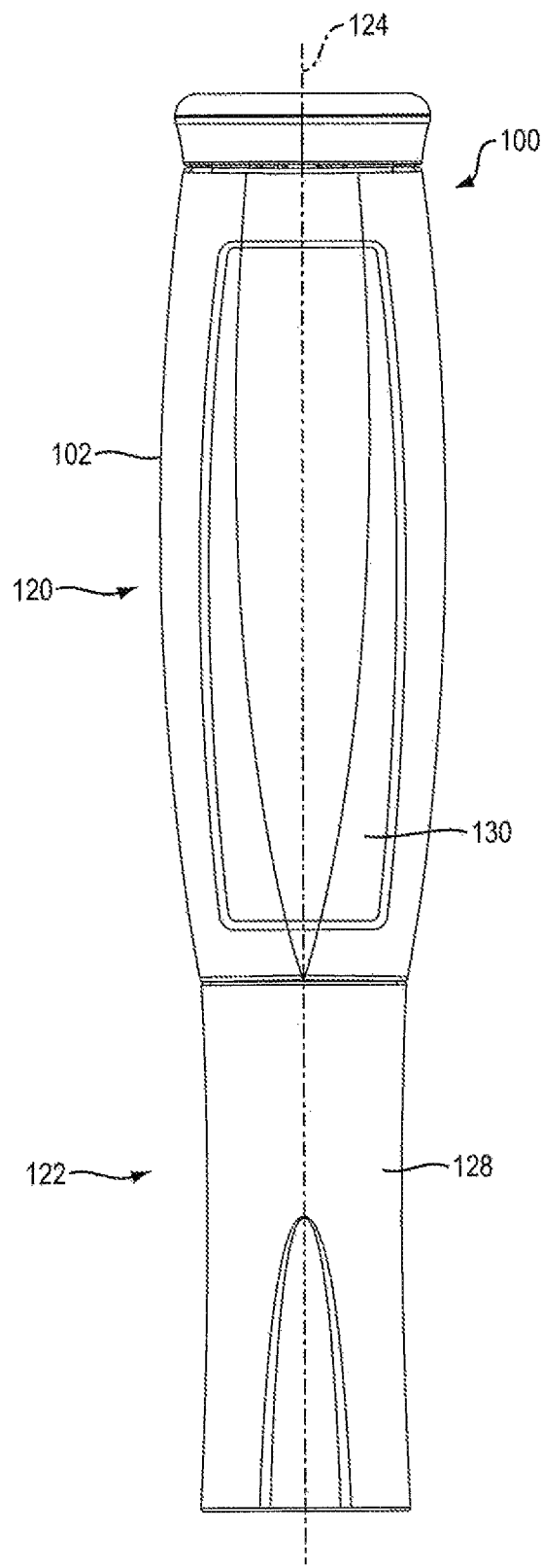
FIG. 14A is a side view of the injection device shown in FIG. 1D.
Figure 14B:
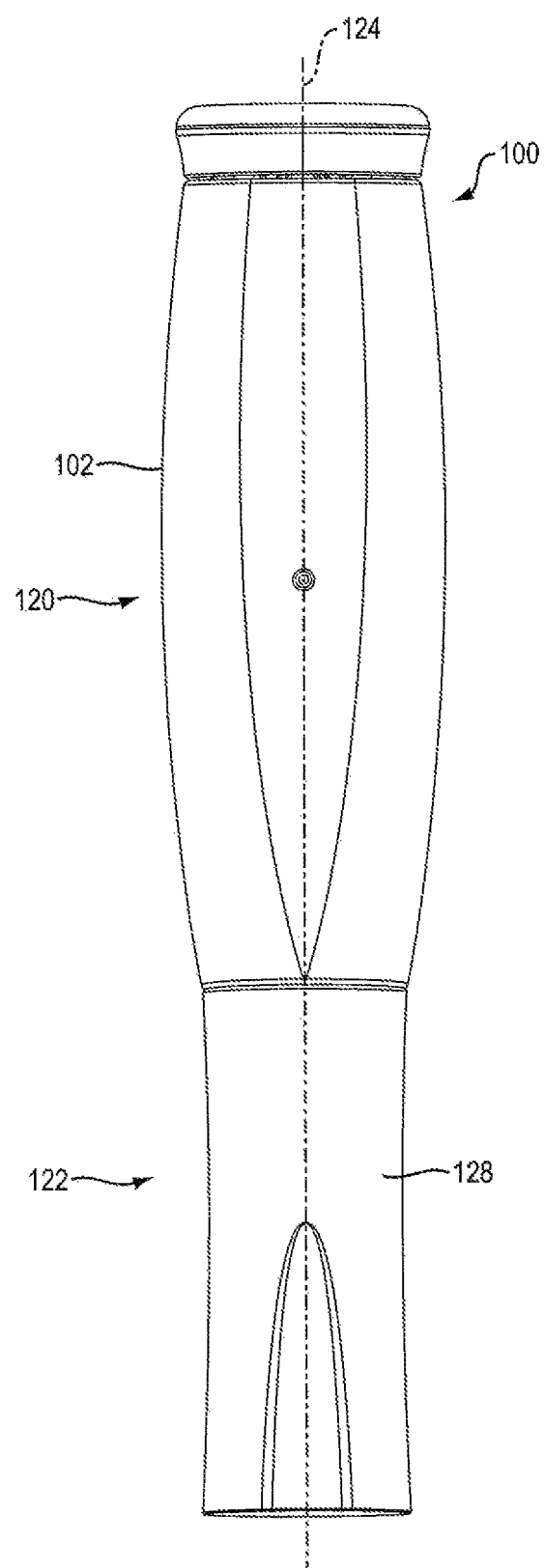
FIG. 14B is a side view of the injection device shown in FIG. 1D.

Referring to FIGS. 1A, 1B, 1C, 1D, 14A, 14B, 15A, and 15B, in certain embodiments, injection device 100 is configured to administer a dose of medicament. In one embodiment, injection device 100 is configured in the shape of a pen, having an elongated, substantially writing instrument-like form, although other forms are within the scope of the invention. Referring to FIGS. 14A and 14B, in one embodiment, injection device 100 includes a removable cap 128 attached to the distal section 122 of the injection device 100 thereto. In one embodiment, injection device 100 is a disposable injection pen, in that after the quantity of medicament contained therein is exhausted by multiple operations of the injection device 100, the injection device 100 is discarded rather than being reset and re-used with a replacement container of medicament. In other embodiments, injection device 100 can be reset and is reusable. In one embodiment, the injection device 100 is a re-usable pen, and that after the quantity of medicament contained therein is exhausted, the injection device can be re-set and a new medicament cartridge installed.

In one embodiment, injection device 100 is configured to administer repeated, successive doses of a medicament. In one embodiment, the medicament is delivered in successive repeated fixed doses. In one embodiment, the medicament is delivered in successive repeated variable doses. In other embodiments, the dosage can be controlled and adjusted. Further, in one embodiment, injection device 100 allows the injection to be administered by individuals that do not have formal training (e.g., self-administered or administered by another individual family member or other caregiver who may not be a formally trained healthcare provider, such as a parent administering a drug to a child). In one embodiment, injection device 100 is triggered by one hand of a user. In one embodiment, injection device 100 is held one hand of a user and triggered by the user's finger or thumb. In one embodiment, injection device 100 is useful in situations where self-injections/caregiver administered injections would be beneficial, including, but not limited to, the injection of a drug to treat osteoporosis, psoriasis, and psoriatic arthritis. In one embodiment, the injection device must administer a full dose prior to being able to reset. In one embodiment, the injection device must fully reset before it is able to be triggered.

The injection device 100 can be used to inject a wide range of drugs. For example, injection device 100 can be used to inject drugs, water soluble medicaments and oil soluble medicaments. Some medicaments that can be used with injector device 100 include parathyroid hormone ("PTH") and various other medications such as exenatide and the like. Injection device 100 can also be used to inject medicaments listed in the Physicians' Desk Reference (PDR®), 67th Edition (2013) (which is herein incorporated by reference in its entirety), and, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antineoplastics, anti-obesity preparations, antiparasitics, antiparkinsonism drugs, antipruritics, antipyretics, antispasmodics and anticholinergics, antitoxoplasmosis agents, antitussives, antivertigo agents, antiviral agents, apomorphine, atropine, biologicals, biosimilars, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, diazepam, dihydroergotamine, epinephrine expectorants and combinations, diuretics, emetics, enzymes and digestants, fertility agents, fluorine preparations, galactokinetic agents, general anesthetic, geriatrics, germicides, glucagon, haloperidol, hematinics, hemorrhoidal preparations, histamine H receptor antagonists, hormones, hydrocholeretics, hyperglycemic agents, hypnotics, immunosuppressives, laxatives, lovenox, mucolytics, muscle relaxants, narcotic antagonists, narcotic detoxification agents, ophthalmological osmotic dehydrating agents, otic preparations, oxytocics, parashypatholytics, parathyroid preparations, pediculicides, peptide drugs, phosphorus preparations, premenstrual therapeutics, psychostimulants, quinidines, radiopharmaceuticals, respiratory stimulants, salt substitutes, scabicides, sclerosing agents, sedatives, sumatriptan, sympatholytics, sympathomimetics, thrombolytics, thyroid preparations, toradol, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®. Some other medicaments that can be used with injector device 100 include Ergocalciferol (Calciferol), diethylstilbestrol, Diprovan (propofol), estradiol valerate, fluphenazine decanoate, fulvestrant, intralipid, liposyn, nandrolone decanoate, nebido, nutralipid, paclitaxel, progesterone, prograf, testosterone cypionate, zuclopenthixol, haloperidol dodecanoate, Enbrel, Humira, Lantus, Epogen (Procrit), Neulasta, Aranesp, Avonex, PEGasys, Rebif, Neupogen, Betaseron, Avastin, Remicade, Herceptin, Erbitux, Recombinate, Cerezyme, NovoSeven, Tysabri, Synagis, Copaxone and Kogenate FS. In certain embodiments, the medicament is dissolved in soybean oil, ethyl oleate, castor oil, sesame oil, safflower oil, arachis oil, polyoxyethylated castor oil (Cremophor® EL), polyoxyl 60 hydrogenated castor oil (HCO-60), cottonseed oil, or thin oil derived from coconut oil.

In some embodiments, the medicament may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with the injection device 100 in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, duboisia hopwoodii, prosanthera striatiflora, kava (piper methysticum), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, proclorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia hopwoodii, prosanthera striatiflora, kava (piper methysticum), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, proclorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

Because of the repeated nature of the dosing of certain types of medicaments, it is beneficial to use a device that aides a patient in self-administration of the doses. Repeat dosing includes repetitive injection of the same dose or variable dose. Medicaments that are administered intradermally, subcutaneously or intramuscularly can be used with the injector. Further, many such medicaments should be delivered in a precise amount to ensure efficacy and to reduce side-effects.

In one embodiment, the medicament includes a recombinant form of parathyroid hormone, e.g., teriparatide. Teriparatide has the following structure:

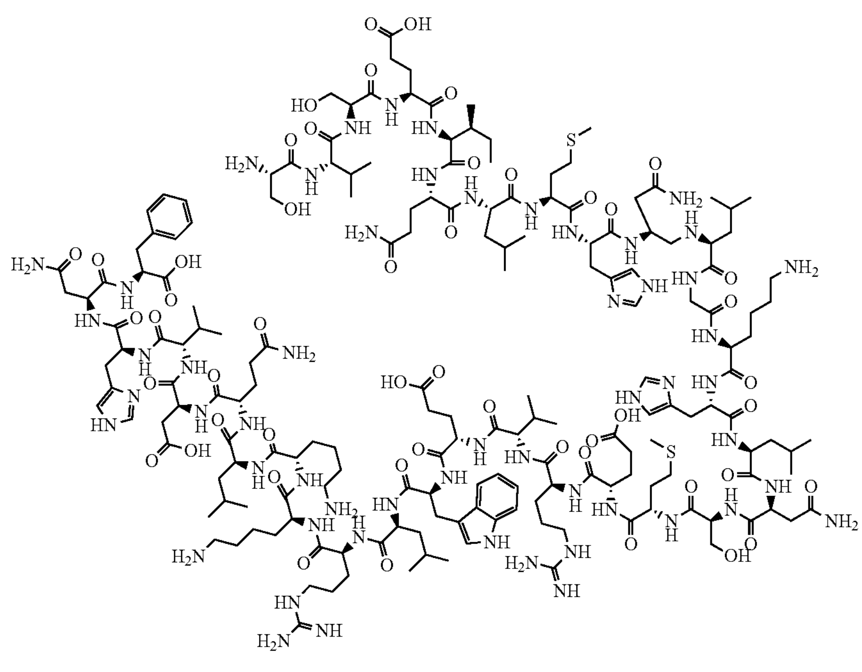

Teriparatide is typically administered by injection once a day in the thigh or abdomen. Teriparatide is indicated for use in postmenopausal women with osteoporosis at a high risk for fracture or with a history of osteoporotic fracture, patients with multiple risk factors for fracture, and for patients who have failed or are intolerant to other available osteoporosis therapy. Teriparatide is also indicated to increase bone mass in men with primary or hypogonadal osteoporosis at high risk of fracture, patients with multiple risk factors for fracture, and for patients who have failed or are intolerant to other available osteoporosis therapy. Teriparatide is indicated as well for the treatment of men and women with osteoporosis associated with sustained systemic glucocorticoid therapy. The typical recommended dose is 20 μg per day. In one embodiment, injection device 100 is configured to administer about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg or any range determinable from the preceding dosage amounts (for example, about 15 μg to about 25 μg or about 1 μg to about 10 μg) of medicament, e.g., Teriparatide, per dose. In one embodiment, injection device 100 is configured to administer about 0.005 mL, about 0.010 mL, about 0.015 mL, about 0.020 mL, about 0.025 mL, about 0.030 mL, about 0.035 mL, about 0.040 mL, about 0.045 mL, about 0.050 mL, about 0.055 mL, about 0.060 mL, about 0.065 mL, about 0.070 mL, 75 μL, about 0.080 mL, about 0.085 mL, about 0.090 mL, about 0.095 mL, about 0.100 mL, about 0.105 mL, about 0.110 mL, about 0.115 mL, about 0.120 mL, about 0.125 mL, about 0.130 mL or any range determinable from the preceding dosage amounts (for example, about 0.025 mL to about 0.045 mL or about 0.005 mL to about 0.130 mL) of medicament, e.g., Teriparatide, per dose.

Referring to FIGS. 1A and 14A, in one embodiment, injection device 100 includes a proximal section 120 and a distal section 122. In one embodiment, distal section 122 contains the medicament to be dispensed at its distal end upon operation of injection device 100. In one embodiment, the proximal section 120 contains the dosage mechanism 126, as shown in FIGS. 3A, 3B, 15A and 15B used to force the contained medicament from the distal end of distal section 122.

In one embodiment, injection device 100 includes housing 102. In one embodiment, housing 102 has a proximal-distal axis 124. In one embodiment, housing 102 of injection device 100 is formed from a light weight material, e.g., an injected molded plastic. In one embodiment, housing 102 is covered in an opaque or elastomeric covering to alter the color, shape or texture of housing 102. In one embodiment, housing 102 is formed of at least two separate parts, e.g., first portion 1020a and second portion 1020b as shown in FIGS. 2A, 2B, 16A and 16B. In one embodiment, the housing parts 1020a and 1020b are aligned via mating pins and recesses provided therein and fixedly secured together during manufacture, such as via adhesives or ultrasonic welding. In one embodiment, the housing parts 1020a and 1020b are fixedly secured together by a mechanical joint system where part-to-part attachment is accomplished with locating and locking features. In one embodiment, housing parts 1020a and 1020b are fixedly secured using clips where said clips can be integral to one or the other or both housing parts. In another embodiment, securing clips are separate from housing parts 1020a and 1020b. In one embodiment, housing 102 is generally elliptical in transverse cross-section to accommodate dosage mechanism 126. In one embodiment, the generally elliptical housing 102 is configured with generally flat surfaces opposing one another on said housing. In one embodiment, housing 102 is configured with flat surfaces sufficient to minimize the potential for the device to roll. In one embodiment, the flat surfaces found as part of elliptical housing 102 are designed to retain internal device components. In one embodiment, the flat surfaces of elliptical housing 102 are designed to retain dosing mechanism 126. In one embodiment, the flat surfaces for housing 102 contain rails and ribs for retaining internal device components. In one embodiment, housing 102 is provided with an external thread or another suitable connections means at a distal portion of the housing 102 to releasably connect a cartridge sleeve 114 thereto. In one embodiment, housing 102 is provided with suitable connection means at a distal portion of housing 102 to adjustably connect the cartridge sleeve 114 thereto.

In one embodiment, injection device distal section 122 includes a cartridge sleeve 114 which can be used to hold a number of differently-sized cartridges. Additionally, a number of differently-sized cartridge sleeves can be provided, as necessary for differently-sized cartridges. In one embodiment, the cartridge sleeve 114 is provided with an internal thread or another suitable connections means at a proximal portion of the cartridge sleeve 114 to releasably connect housing 102 thereto. In one embodiment, cartridge sleeve 114 is provided with suitable connection means at its proximal end to adjustably connect the cartridge sleeve 114 to housing 102 thereto. In one embodiment, the cartridge sleeve 114 is reversibly connected to housing 102. In one embodiment, the reversible connection of cartridge sleeve 114 to housing 102 allows replacement of medicament cartridge 112 and re-setting of device 114.

In one embodiment, cartridge sleeve 114 is provided with an external thread 118 or another suitable connections means 118 at a distal portion of cartridge sleeve 114 to releasably connect a pen-needle assembly thereto.

In one embodiment, a pen-needle assembly (not shown) is of known design and includes a double-ended needle cannula or injection needle. In one embodiment, the pen-needle assembly consists of an injection needle mounted in a tubular hub that is internally threaded to cooperate with the external thread 118 of cartridge sleeve 114 so as to be reversibly attached to the external threading of the cartridge sleeve 114. Other types of connection types, including a snap on connection, may be provided between the needle assembly and the cartridge sleeve 114. In one embodiment, the injection needle is fitted with a protective cover, e.g, a needle cap, thereover to protect those handling or who may otherwise encounter injection device 100. In one embodiment, the pen-needle assembly is a single injection needle. Various types of other needle assemblies known in the art may be used with injection device 100, including, but not limited to, assemblies with one or more shortened injection needles, including microneedle arrays, pen needle assemblies incorporating sharps protection or assemblies compatible with or connectable to intravenous lines or the like including needle-free blunt connections.

In one embodiment, injection device 100 includes a cartridge 112. In one embodiment, cartridge 112 is of the type typically used in connection with injection devices, e.g., needled injector devices, and is formed of glass or certain types of plastic that have qualities that are necessary for storage of liquid medicament. Such qualities can include low air permeation, lubricity, low leeching of chemicals and corrosion resistance. In one embodiment, cartridge 112 is generally cylindrical in shape and can have a diameter configured to fit within cartridge sleeve 114, although other shapes can be used. In one embodiment, cartridge 112 and cartridge sleeve 114 are engage at an interface. In one embodiment, an adhesive is applied at the interface of cartridge 112 and cartridge sleeve 114. In one embodiment, the adhesive is light cured. In one embodiment, the cartridge 112 defines a medicament-filled reservoir that is closed at its proximal end by a plunger 110 that is axially slideably and sealably engaged with the cartridge interior wall to hold the medicament within the reservoir. In one embodiment, the distal, outlet end of the cartridge reservoir is sealed by a septum held by a cap that is secured to a stepped-down diameter neck portion of the cartridge 112. In one embodiment, the septum cap secured to the stepped-down diameter neck of the cartridge 112 is secured in the stepped down distal end of the cartridge sleeve 114 around which external threads 118 are present. In one embodiment, when the pen-needle assembly is mounted on cartridge sleeve 114, a proximal point of an injection needle penetrates the cartridge septum to provide a fluid flow outlet by which medicament within the cartridge reservoir can be dispensed from a needle tip during operations of injection device 100. In one embodiment, cartridge 112 is configured to contain a predetermined amount of a medicament. The predetermined amount of medicament that the cartridge is configured to contain can vary with the medicament injected and with the recommended dose size for the particular medicament and the patient. In one embodiment, distally advancing plunger 110 causes the volume of the cartridge reservoir to decrease and an amount of liquid medicament to expel from the injection needle in an amount that corresponds to the reduction in volume caused by the movement of the plunger.

To reliably provide repeated small doses of a liquid medicament, in one embodiment, cartridge 112 is constructed to hold a predetermined number of doses. In one embodiment, the doses in cartridge 112 correspond to a predetermined period of medicament administration. In one embodiment, cartridge 112 is constructed to hold a predetermined volume of medicament. In one embodiment, the doses in cartridge 112 include sufficient medicament for purging air from the cartridge 112 and medicament to correspond to a predetermined period of medicament administration. In one embodiment, the medicament in the cartridge is sufficient for purging air from the cartridge, allow for practice injections, correspond to a predetermined period of medicament administration and allow for residual medicament assuring the last dose of medicament is a complete dose. For example, in one embodiment, injector device 100 is intended for use with a teriparatide solution that is to be administered once daily and sufficient drug is provided for the prescribed treatment over a pre-determined number of successive days at a dose of 0.08 mL administered through movement of a plunger 110 a distance of about 1.1 mm. For example, in one embodiment, injector device 100 is intended for use with a teriparatide solution that is to be administered once daily for twenty eight successive days at a dose of 0.08 mL administered through movement of a plunger 110 a distance of about 1.1 mm. In one embodiment, the injector device 100 is configured to administer a dose of medicament, e.g., teriparatide, once daily for 1 day, 2 successive days, 3 successive days, 4 successive days, 5 successive days, 6 successive days, 7 successive days, 8 successive days, 9 successive days, 10 successive days, 11 successive days, 12 successive days, 13 successive days, 14 successive days, 15 successive days, 16 successive days, 17 successive days, 18 successive days, 19 successive days, 20 successive days, 21 successive days, 22 successive days, 23 successive days, 24 successive days, 25 successive days, 26 successive days, 27 successive days, 28 successive days, 29 successive days, 30 successive days, 31 successive days, 32 successive days, 33 successive days, 34 successive days, 35 successive days, 36 successive days, 37 successive days, 38 successive days, 39 successive days, 40 successive days, or any range determinable from the preceding days (for example, 3 successive days to 5 successive days or 25 successive days to 35 successive days).

In one embodiment, cartridge 112 is configured to contain about 3 mL of teriparatide. In one embodiment, cartridge 112 is configured to contain about 2.7 mL of teriparatide. In one embodiment, cartridge has a diameter of about 12 mm and a height of approximately 64 mm to contain 3 mL of medicament, although other dimensions can be used to achieve the desired accuracy. In another embodiment, cartridge 112 has a diameter of about 12 mm and a height of approximately 64 mm to contain about 2.7 mL of medicament, although other dimensions can be used to achieve the desired accuracy. Cartridges 112 containing more or less medicament can be provided and can vary in diameter, height or both. In one embodiment, cartridge 112 is configured to hold between about 0.5 mL, 1.0 mL, about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, about 10.0 mL or any range determinable from the preceding amounts (for example, about 2 mL to about 5 mL or 3.0 mL to about 9.5 mL) of liquid medicament. In one embodiment, injection device 100 is configured to dispense different amounts of liquid medicament per dose. Further, the overall volume can be increased to include a predetermined amount of additional volume that remains in cartridge 112 when the intended dosing is complete. This can reduce the likelihood of an incomplete final dose or the presence of air in an injection.

With additional reference to FIGS. 1B, 1C, 3A and 3B, 15A, 15B, 17A and 17B, proximal section 120 of injection device 100 contains the dosage mechanism 126 which is configured to cause movement of plunger 110 contained in cartridge 112 a predetermined dosing distance. This movement may occur in successive increments and such successive increments may correspond to the number of doses to be administered. In one embodiment, dosage mechanism 126 includes a ram 108, a ratchet gear 116, a crank arm 106 and a user-manipulable push button 104.

Figure 4:
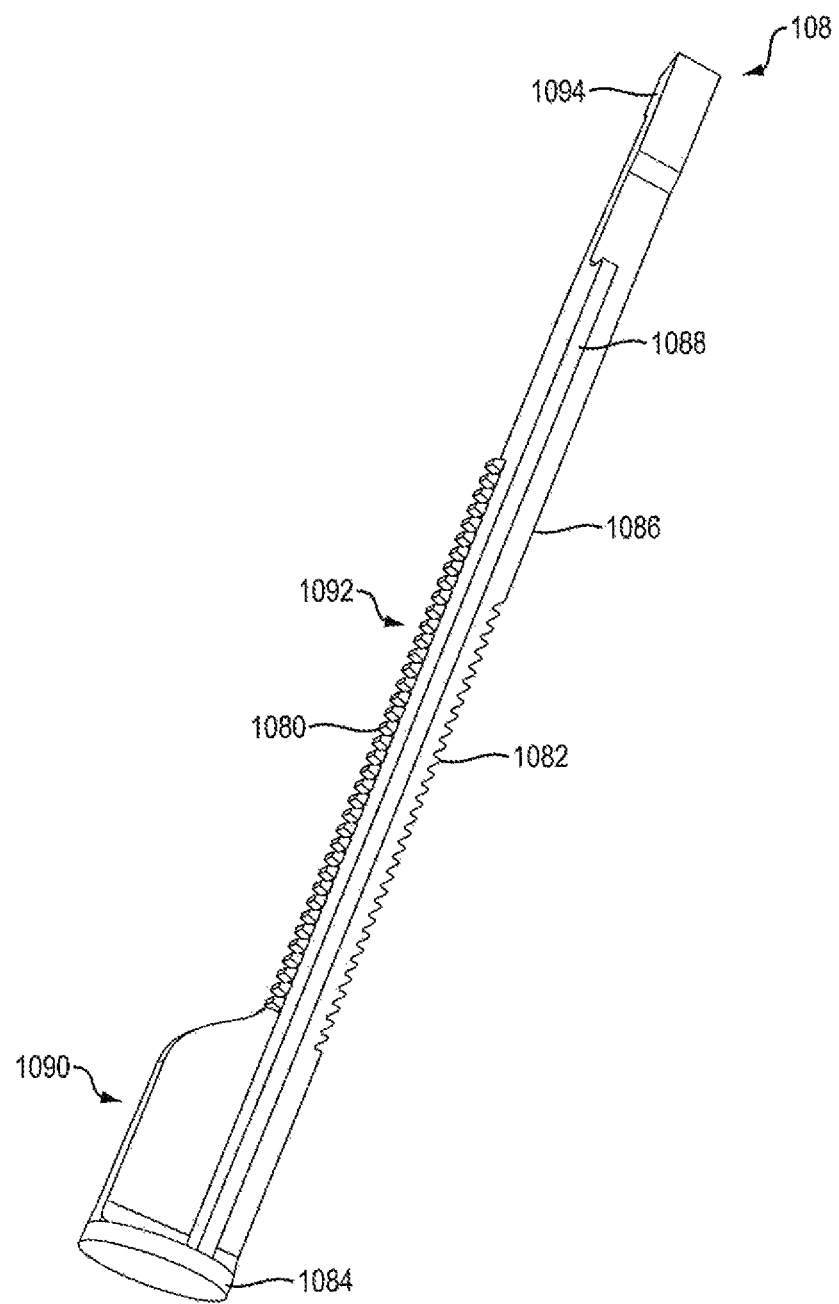
FIG. 4 is a side view of a ram of the injection device shown in FIG. 1A.
Figure 13D:
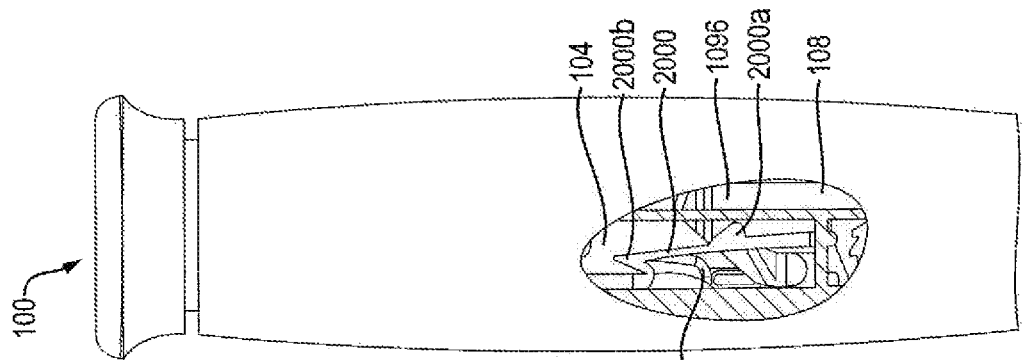
FIGS. 13A, 13B, 13C, and 13D are partial side cutaway views of a lock-out feature of the injection device shown in FIG. 1D.
Figure 13C:
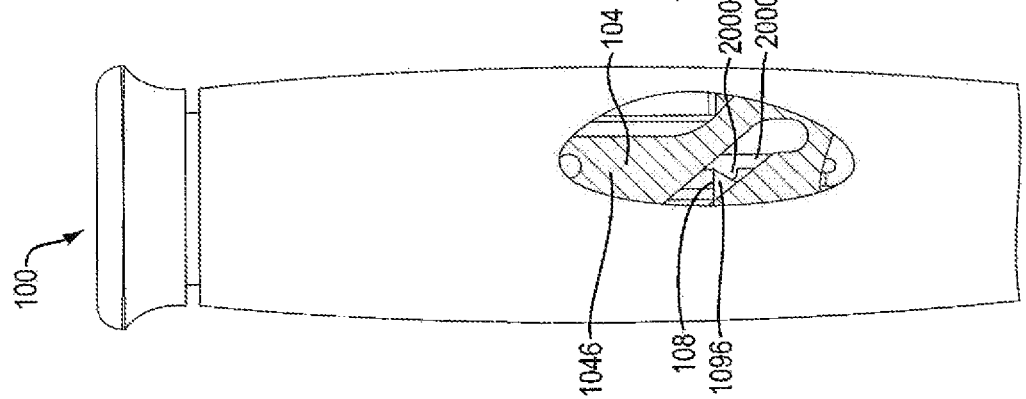
Figure 13B:
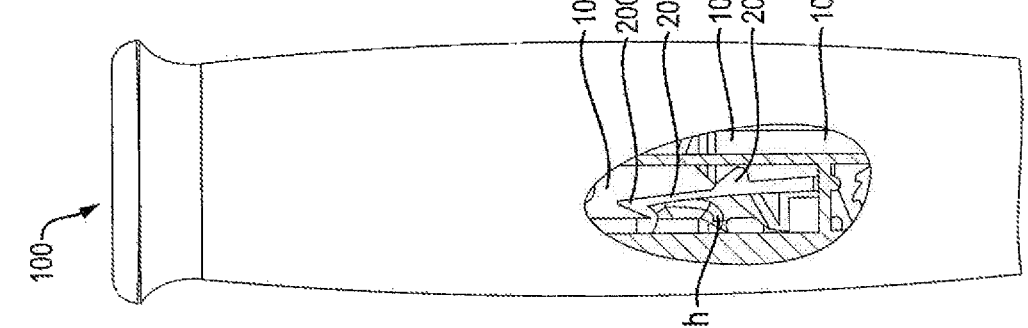
Figure 13A:
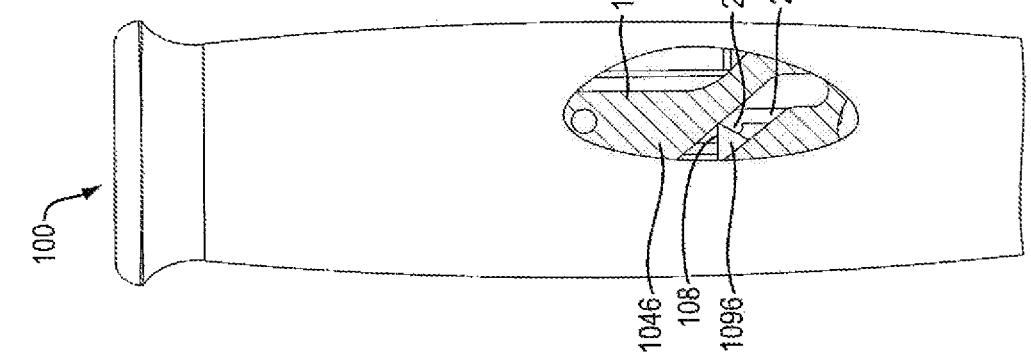
Figure 18:
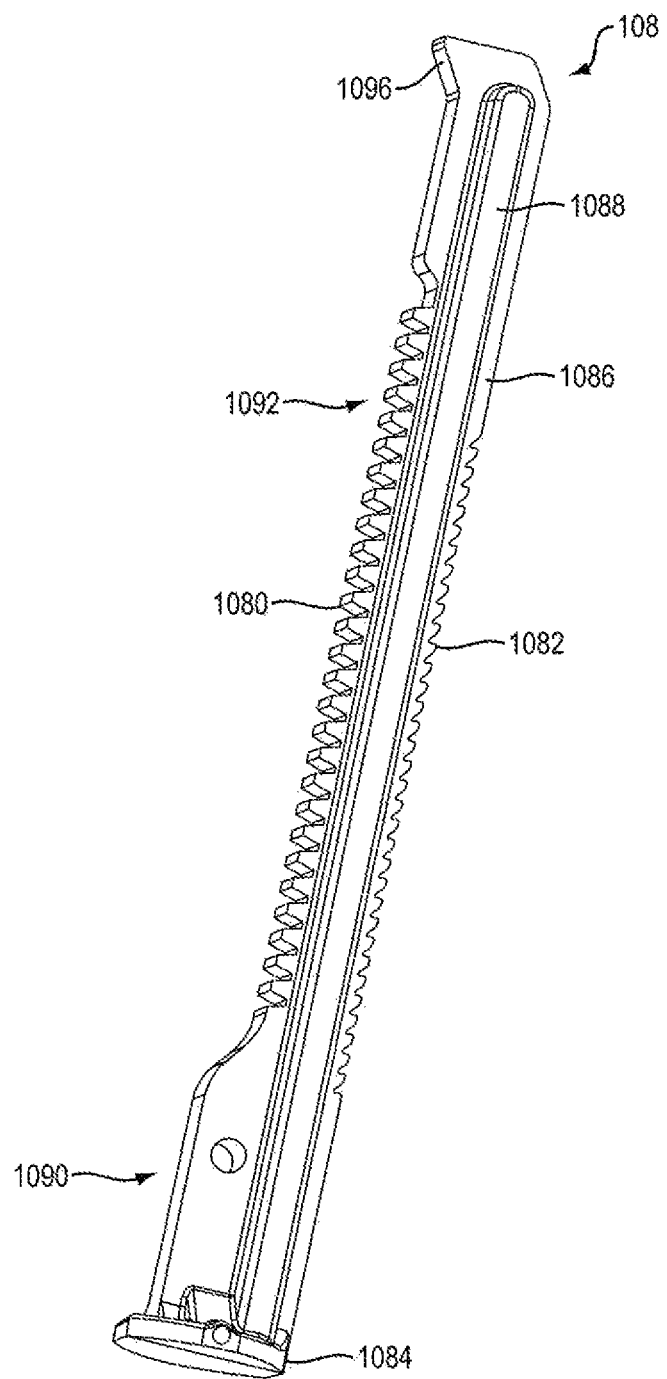
FIG. 18 is a side view of a ram of the injection device shown in FIG. 1D.

Referring to FIGS. 4 and 18, in one embodiment, ram 108 has a foot 1084, a shaft 1086, and a support bar 1088. In one embodiment, foot 1084 is at a distal end of shaft 1086 and includes a planar surface. In one embodiment, the planar surface is circular. In one embodiment, foot 1084 has a larger surface area than any transverse cross-sectional area of the shaft 1086 to distribute loading on the cartridge plunger 110 that foot 1084 contacts and thereby directly engages cartridge plunger 110 during advancement. In one embodiment, shaft 1086 has a distal portion 1090 having a larger transverse cross-sectional area than a transverse cross-sectional area of a proximal portion 1092 to distribute loading on the foot 1084. In one embodiment, shaft 1086 is not axially aligned with the center of foot 1084. In one embodiment, ram 108 includes a lock out protrusion 1094 (as shown in FIG. 4) or a lock out protrusion 1096 (as shown in FIGS. 13A, 13B, and 18) that extends from a proximal end of shaft 1086 configured for use with a lock-out feature (described in more detail below). In one embodiment, shaft 1086 has at least two sets of teeth, gear engaging teeth 1080 and pawl engaging teeth 1082 axially disposed along opposing sides of a portion of shaft 1086. In one embodiment, the geometry of gear engaging teeth 1080 matches the geometry of pinion teeth 1162 on ratchet gear 116 (discussed in more detail below). The pawl engaging teeth 1082 are spaced apart linearly according to the dose travel amount. In one embodiment, pawl engaging teeth 1082 include a pressure angle. In one embodiment, the pressure angle of pawl engaging teeth 1082 is axially aligned with the plunger axis. In another embodiment, support bar 1088 is axially disposed along a portion of shaft 1086. In another embodiment support bar 1088 is configured to interact with second portion of housing 1020*b* In another embodiment, support bar 1088 is on shaft 1086 to provide stiffness to the part.

Figure 2A:
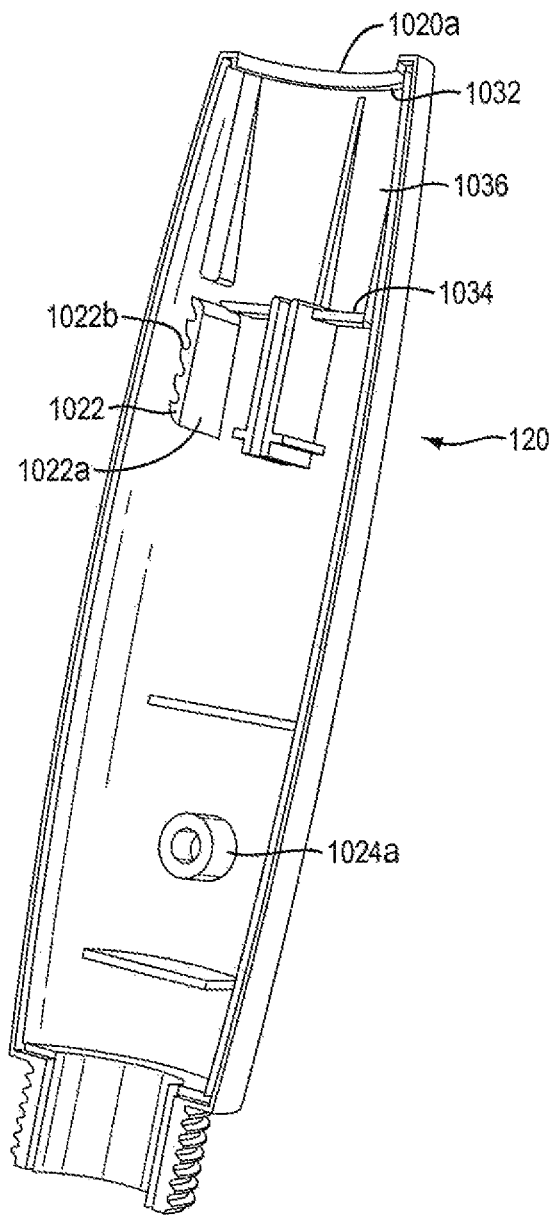
FIG. 2A is a side view of a first portion of housing of the injection device shown in FIG. 1A.
Figure 2B:
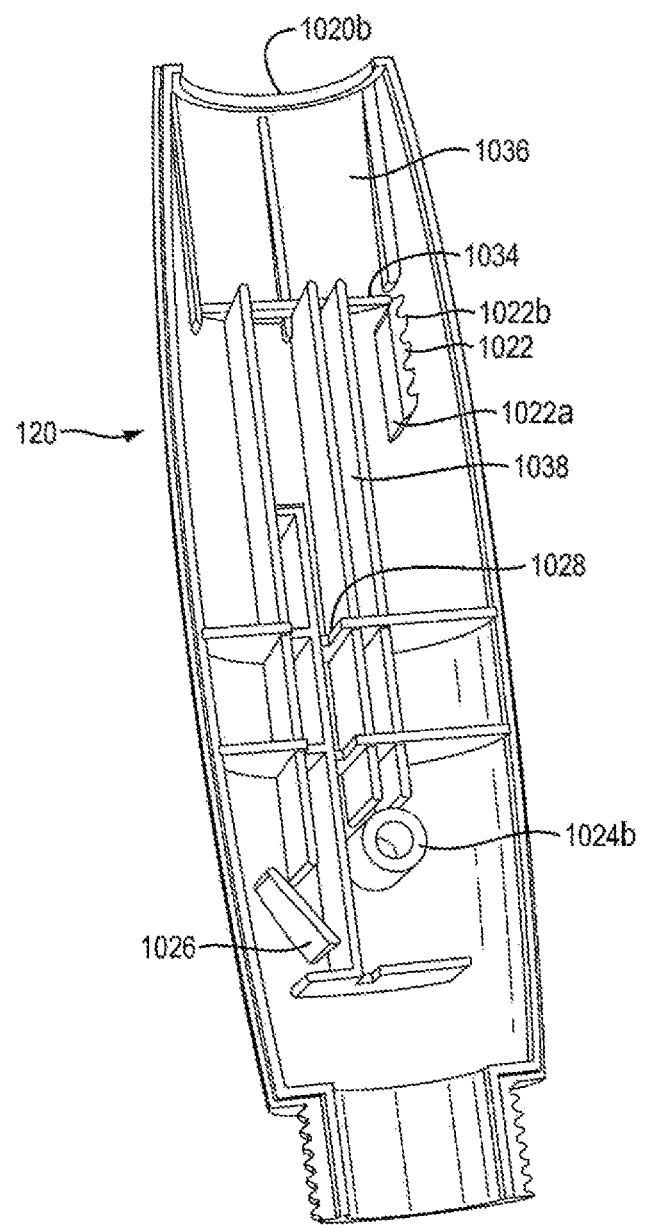
FIG. 2B is a side view of a second portion of housing of the injection device shown in FIG. 1A.
Figure 5:
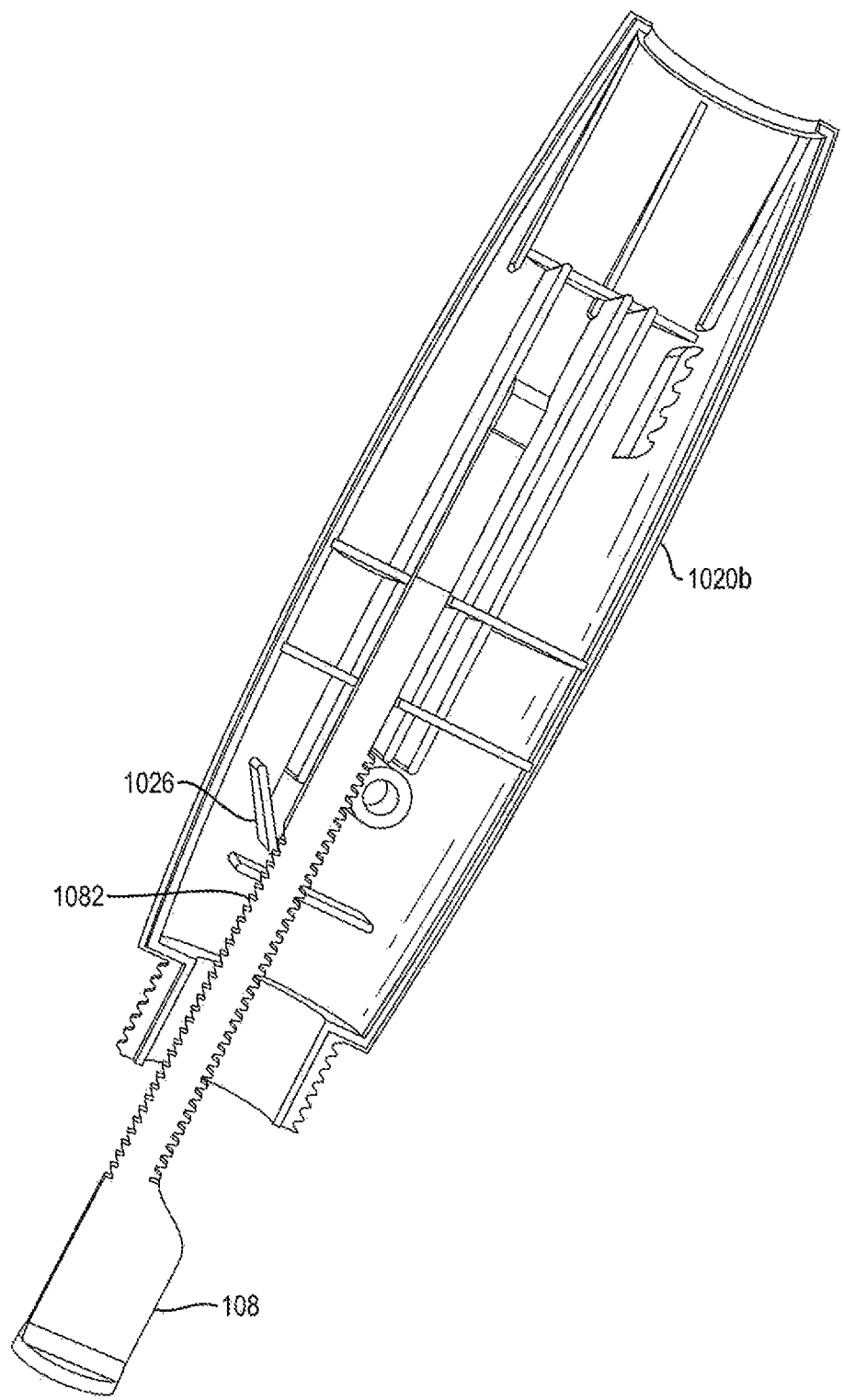
FIG. 5 is a side view of a ram and a second portion of housing of the injection device shown in FIG. 1A.
Figure 16A:
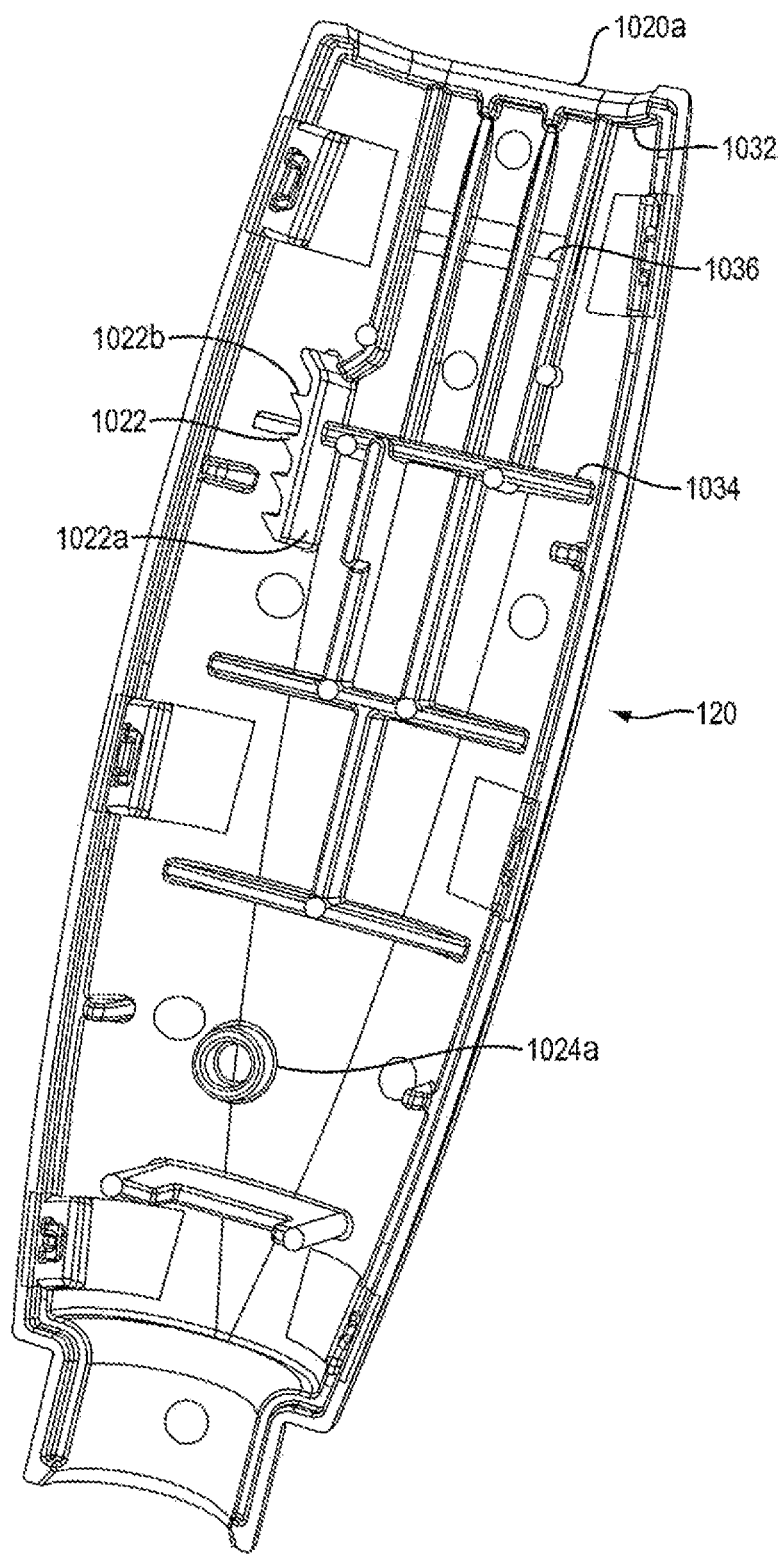
FIG. 16A is a side view of a first portion of housing of the injection device shown in FIG. 1D.
Figure 16B:
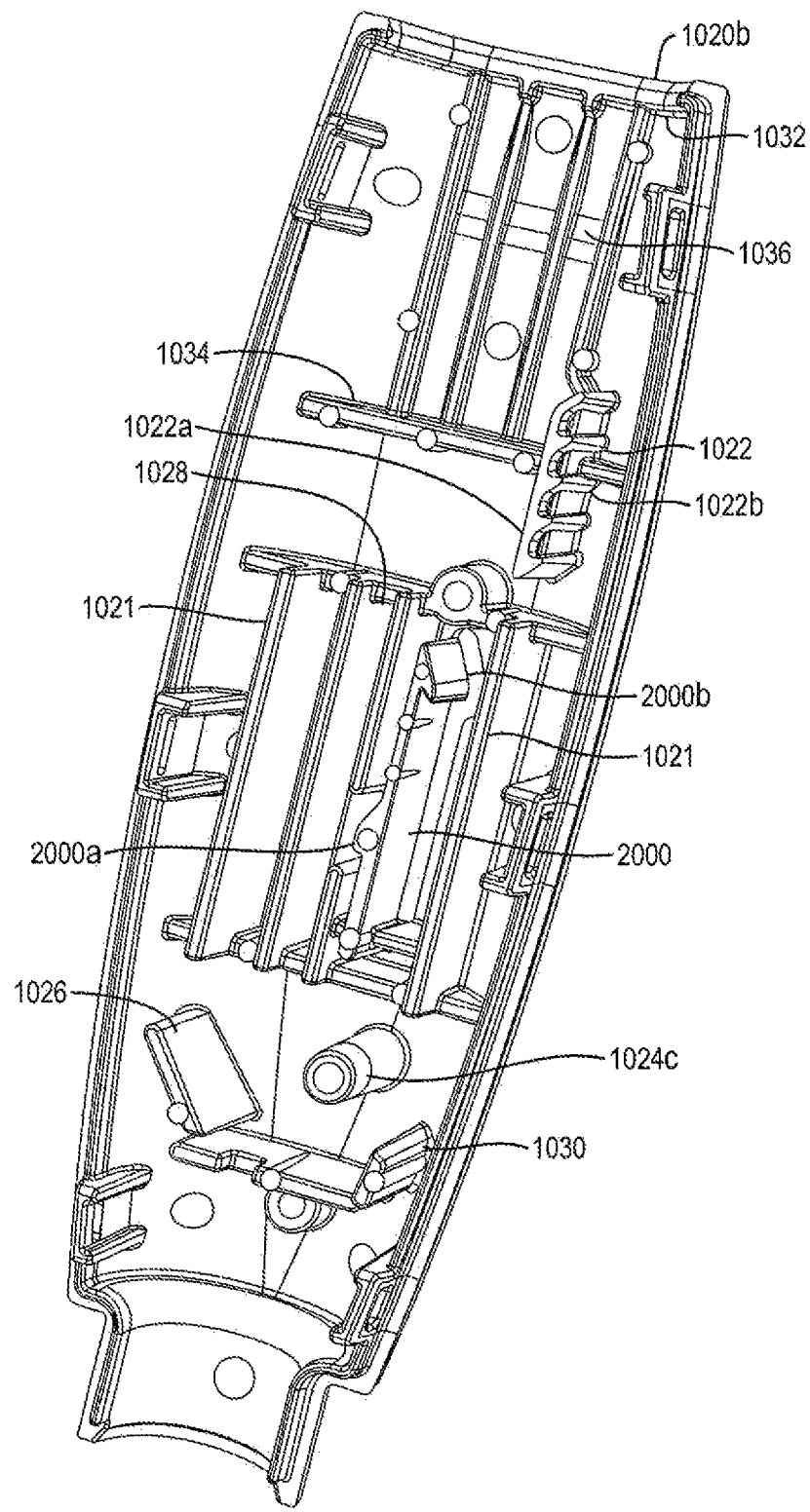
FIG. 16B is a side view of a second portion of housing of the injection device shown in FIG. 1D.
Figure 19:
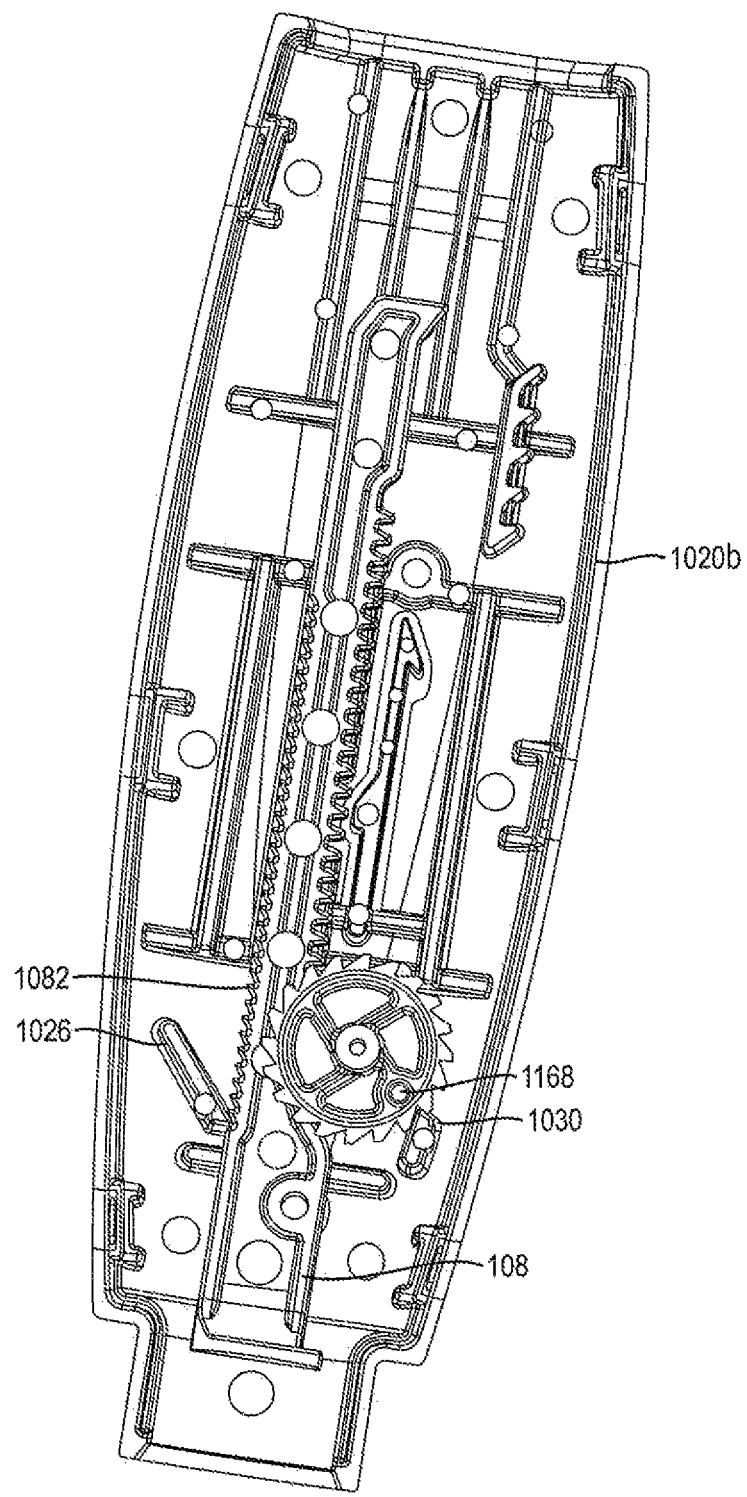
FIG. 19 is a side view of a ram and a second portion of housing of the injection device shown in FIG. 1D.

Referring to FIGS. 5 and 19, in one embodiment, ram 108 is constrained by the internal shaping of the housing 102 to be axially translatable and rotatably fixed therein. As shown in FIGS. 2B and 16B, in one embodiment, second portion of housing 1020*b* has a support bar receiving slot 1028 which is configured to hold support bar 1088 of ram 108 to prevent rotation and allow axial translation of the ram 108. In certain embodiments, lateral or rotational ram movement disengages the pinion teeth 1162. In one embodiment, ram 108 is movable in the distal direction and prevented from proximal movement relative to the housing 102. As shown in FIGS. 5 and 19, in one embodiment, pawl engaging teeth 1082 are employed with a portion of housing 102 to provide for these one-way axial motions.

In one embodiment, pawl engaging teeth 1082 are provided with a one-way ramping, and are engageable with a pawl 1026, which is integrally formed within in the second portion of housing 1020*b* and functions within housing 102. In one embodiment, ram teeth 1082 slide over pawl 1026 as the ram 108 is moved distally during injection, but pawl 1026 abuts pawl engaging teeth 1082 upon proximal movement of ram 108. In one embodiment, pawl 1026 is in interference with and presses ram 108 such that gear engaging teeth 1080 are in close contact with pinion teeth 1162. In one embodiment, pawl engaging teeth 1082 are equal in length, resulting in ram travel being of equal length per stroke and resulting in a single or fixed dose injection device. In a multiple dose, fixed dose embodiment, pawl engaging teeth 1082 are of unequal in length, resulting in unequal ram travel per stroke.

Figure 3A:
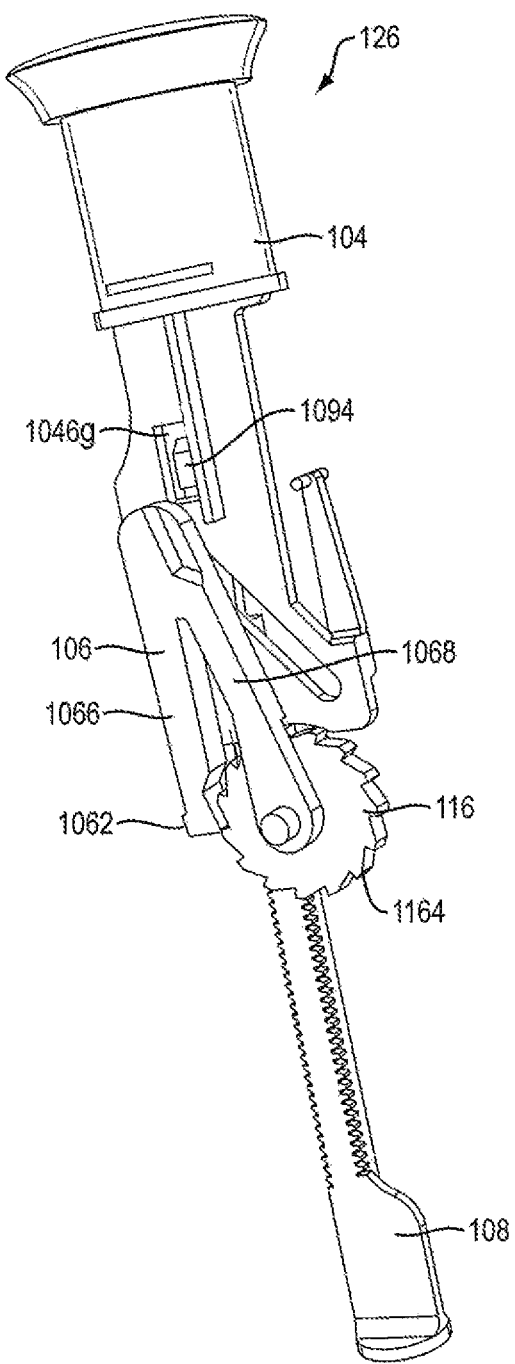
FIG. 3A is a front side view of a dosage mechanism of the injection device shown in FIG. 1A.
Figure 3B:
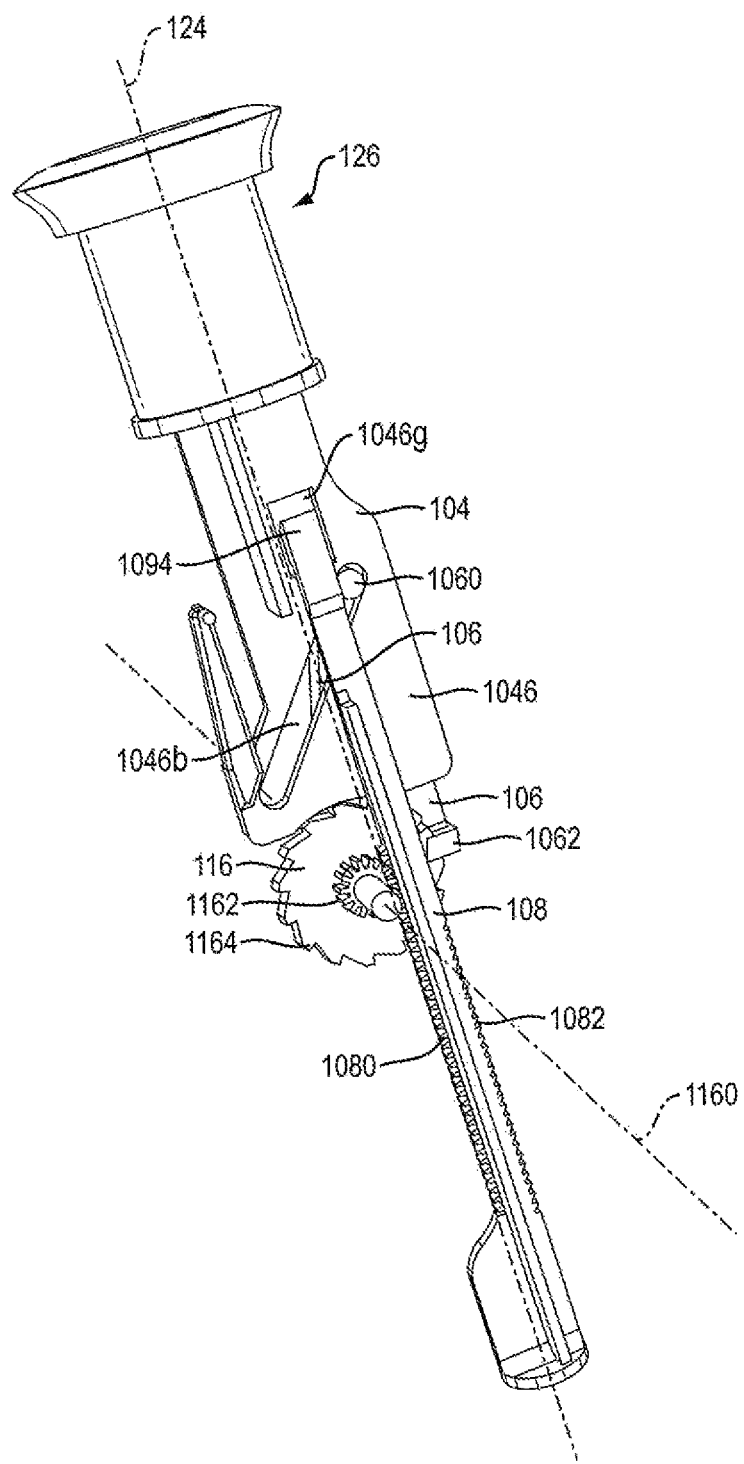
FIG. 3B is a rear side view of a dosage mechanism of the injection device shown in FIG. 1A.
Figure 17A:
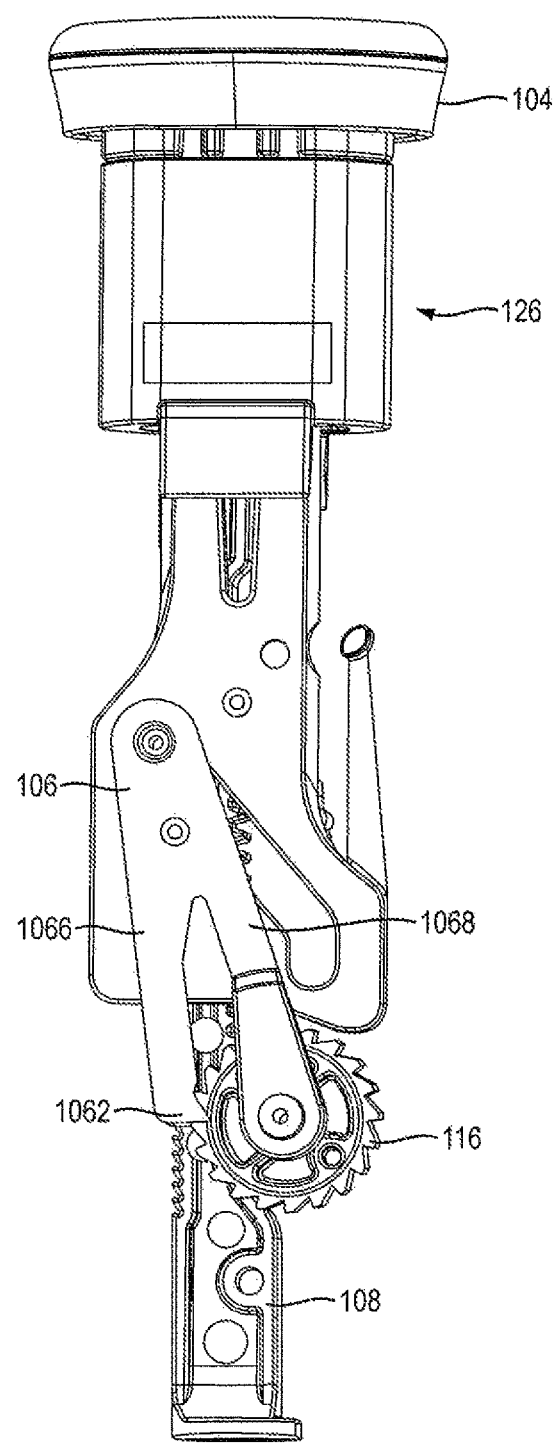
FIG. 17A is a front side view of a dosage mechanism of the injection device shown in FIG. 1D.
Figure 17B:
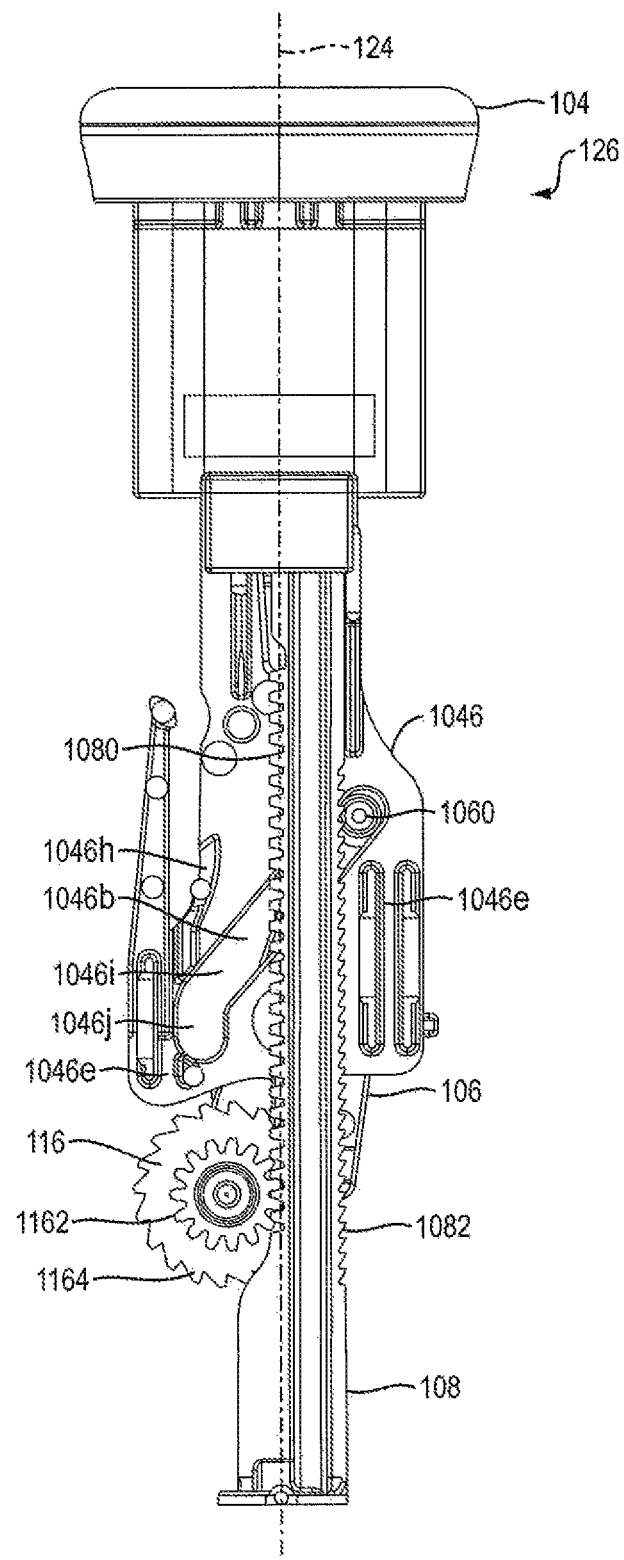
FIG. 17B is a rear side view of a dosage mechanism of the injection device shown in FIG. 1D.

Referring to FIGS. 3B and 17B, in one embodiment, gear engaging teeth 1080 are engageable with ratchet gear 116. In one embodiment, pinion teeth 1162 and ratchet teeth 1164 are in one component connected through axis 1160. In one embodiment, the ratchet teeth 1164 are spaced at a predetermined angle. In one embodiment, the pinion teeth 1162 have a predetermined pitch diameter and involute gear teeth geometry. In one embodiment, the combination of the angular rotation of the ratchet gear 116, the pinion teeth 1162 and the gear engaging teeth 1080 on the ram 108 control the dosage amount. Ram 108 is shown in FIGS. 4 and 18 as being integrally provided with its gear engaging teeth 1080 and pawl engaging teeth 1082, such as by being made of a one-piece plastic injection molding, or a one-piece metal part. Other constructions of ram 108, such as an assembly of separately formed component parts, are within the scope of the invention.

Figure 6:
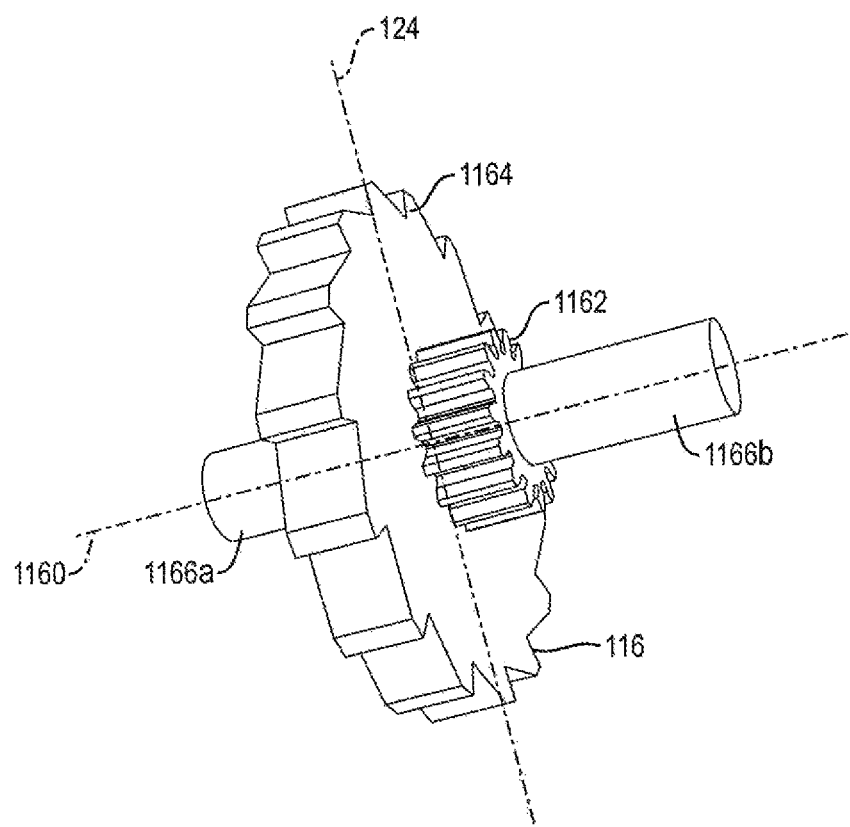
FIG. 6 is a perspective view of a ratchet gear of the injection device shown in FIG. 1A.
Figure 20:
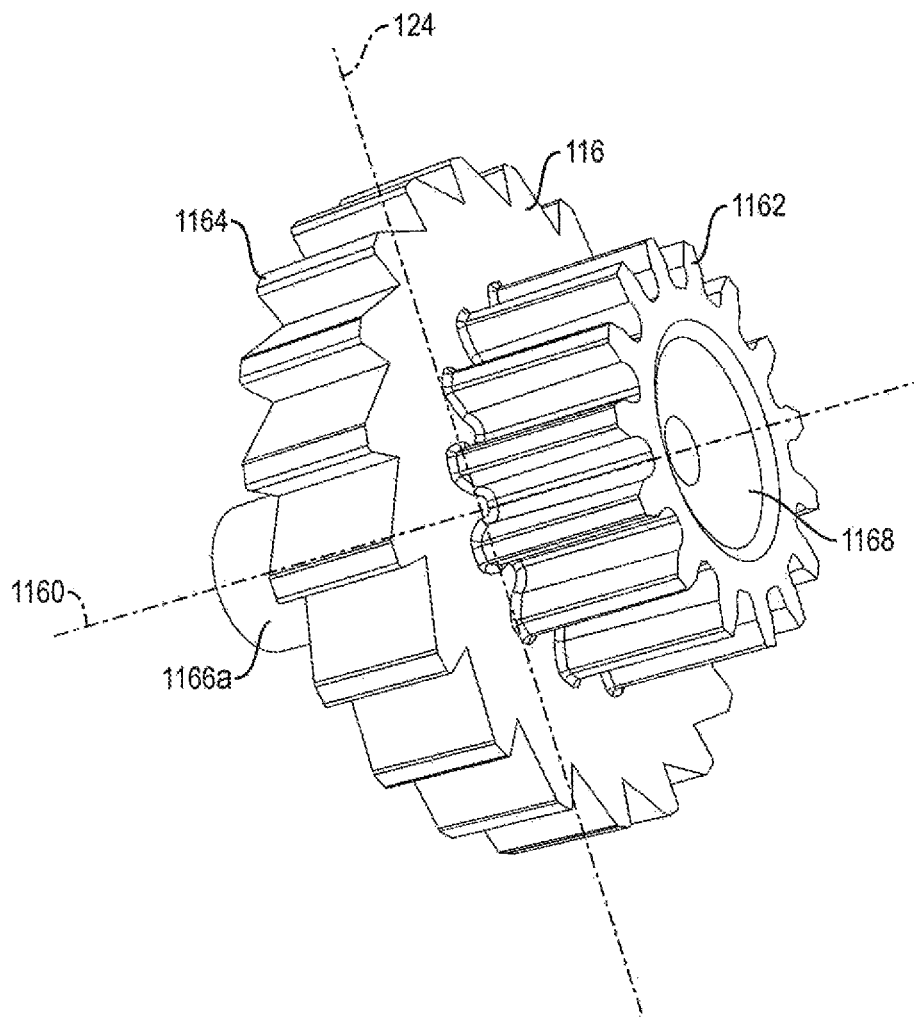
FIG. 20 is a perspective view of a ratchet gear of the injection device shown in FIG. 1D.

Referring to FIGS. 3A, 3B, 17A and 17B, in one embodiment, the dosage mechanism 126 includes a ratchet gear 116. In one embodiment, ratchet gear 116 is centered longitudinally within injection device 100. In one embodiment, ratchet gear 116 is not centered longitudinally within injection device 100. As shown in FIG. 6, in one embodiment, ratchet gear 116 includes housing engagement members 1166*a* and 1166*b* and two sets of gear teeth, pinion teeth 1162 and ratchet gear teeth 1164. In one embodiment, housing engagement member 1166*a* defines an axis 1160 for rolling rotation of ratchet gear 116. In one embodiment, as shown in FIG. 20, ratchet gear 116 includes a recess 1168 (rather than housing engagement member 1166*b*), which is configured to couple with housing mating pin 1024*c* (as shown in FIG. 16B) disposed on the internal surface of house part 1020*b* to aid in preventing axial translation and allowing rotation of the ratchet gear about axis 1160. In one embodiment, axis 1160 is perpendicular to axis 124. In one embodiment, ratchet gear 116 is constrained by the internal shaping of the housing 102 to be rotatable about axis 1160 and axial fixed therein. In one embodiment, housing parts 1020*a* and 1020*b* have ratchet gear engagement members 1024*a* and 1024*b* which are configured to engage housing engagement members 1166*a* and 1166*b* of ratchet gear 116, respectively, to prevent axial translation and allow rotation of the ratchet gear about axis 1160. In one embodiment, ratchet gear 116 includes housing engagement members 1166*a* and 1166*b* configured to engage protrusions of housing parts 1020*a* and 1020*b*, such configuration preventing axial translation and allowing rotation of the ratchet gear about axis 1160.

Figure 1B:
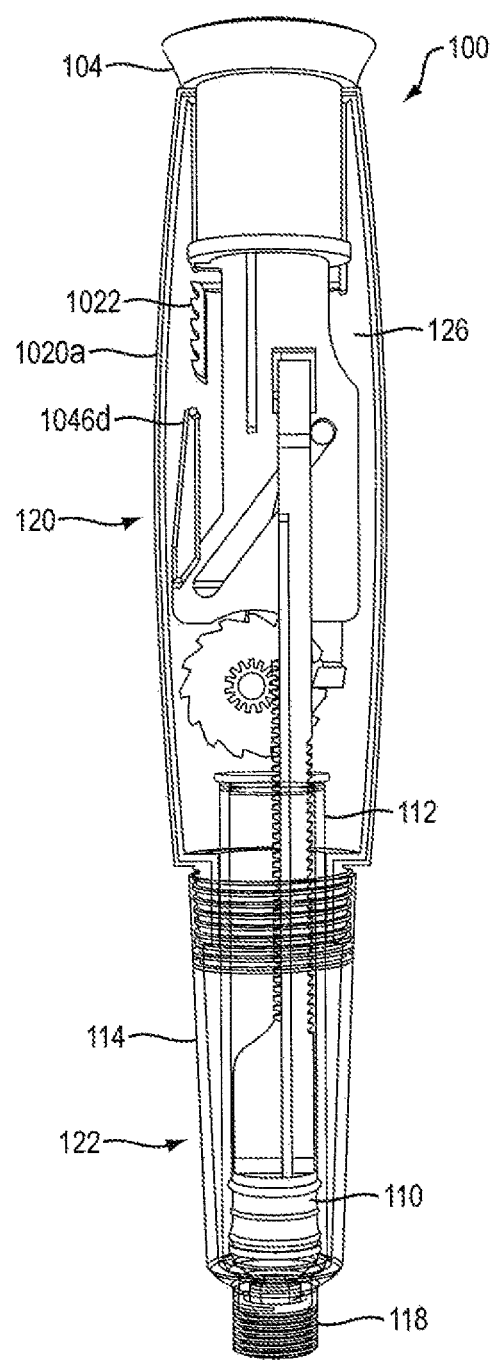
FIG. 1B is a cross-sectional rear side view of the injection device shown in FIG. 1A.
Figure 15A:
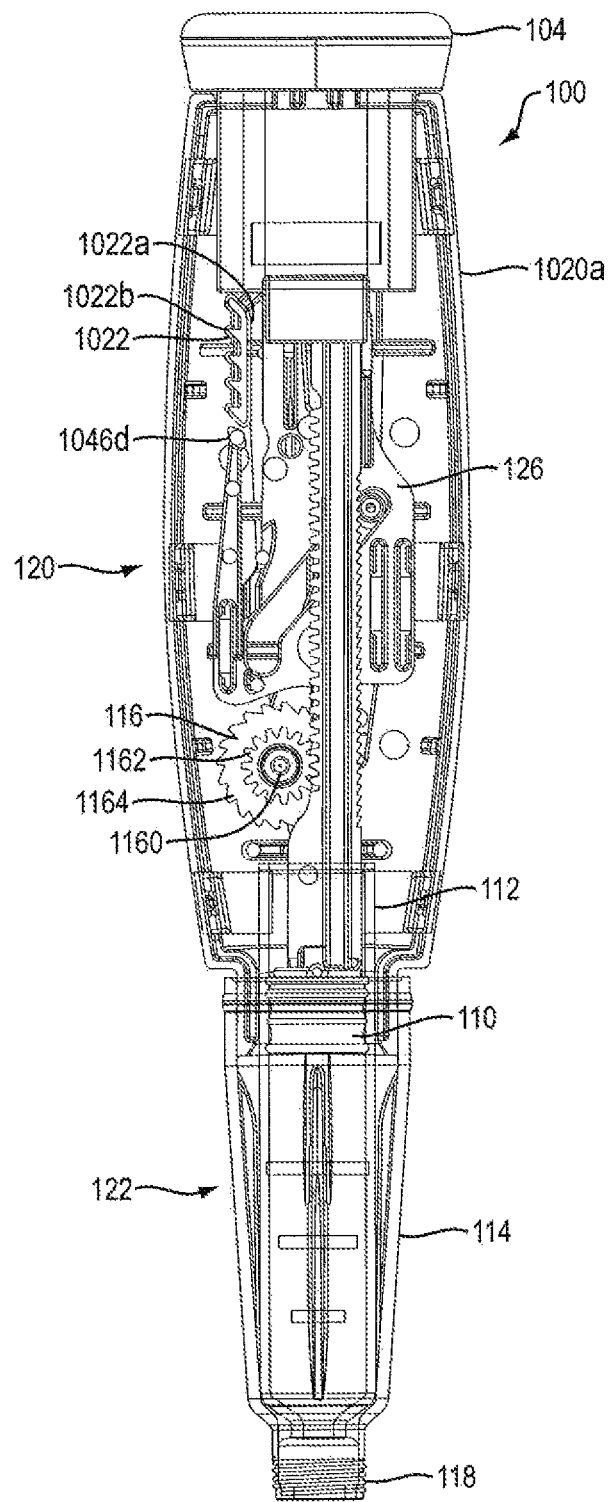
FIG. 15A is a cross-sectional rear side view of the injection device shown in FIG. 1D.
Figure 15B:
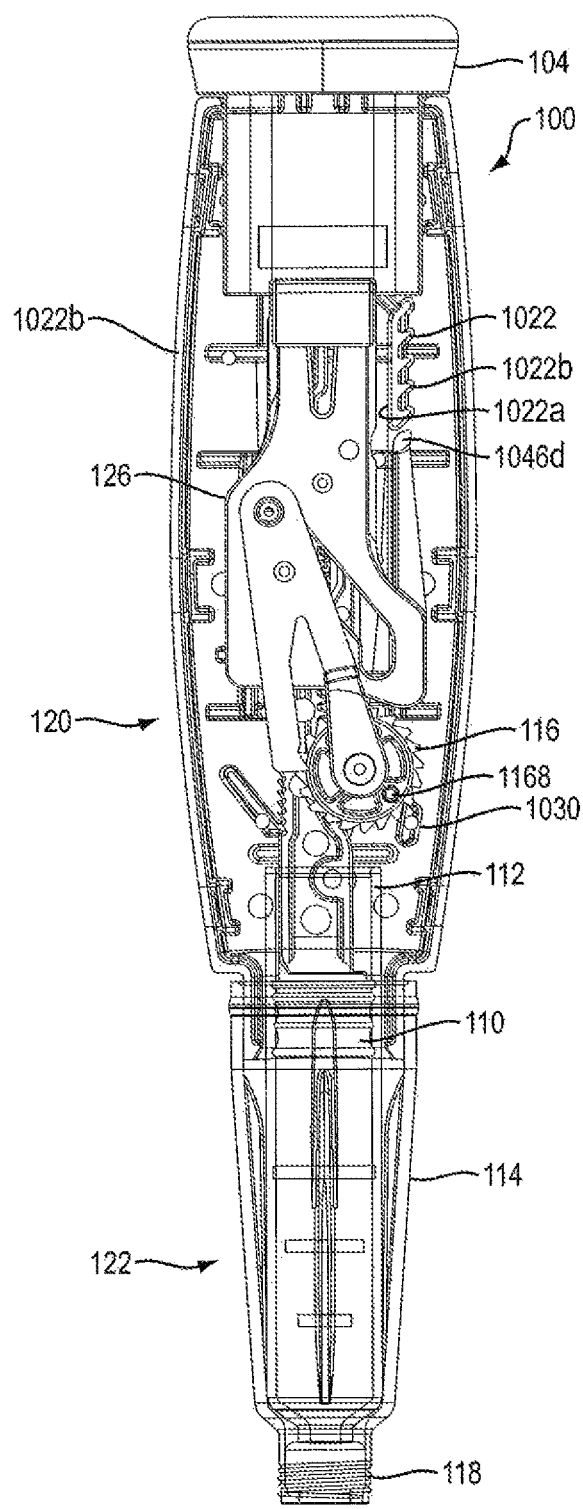
FIG. 15B is a cross-sectional front side view of the injection device shown in FIG. 1D.

Referring to FIGS. 1B and 15A, in one embodiment, pinion teeth 1162 are a continuous ring of teeth that are configured to engage gear engaging teeth 1080 of ram 108 such that as ratchet gear 116 rotates about axis 1160, ram 108 axially advances. In one embodiment, the ratchet gear teeth 1164 are a continuous ring of teeth that are configured to engage a crank arm 106. In one embodiment, ratchet gear teeth 1164 have one-way ramping. In one embodiment, the diameter of pinion teeth 1162 is smaller than the diameter of ratchet gear teeth 1164. In one embodiment, the number of teeth in pinion teeth 1162 is less than the number of teeth in ratchet gear teeth 1164. In one embodiment, there are 15 pinion teeth 1162. In another embodiment, there are 20 ratchet gear teeth 1164. Although pinion teeth 1162 and ratchet teeth 1164 are shown integrally formed in FIG. 6, these components can be separately formed and assembled together so as to be co-rotatable. In one embodiment, ratchet gear 116 moves forward by turning counterclockwise to dispense medicament. In another embodiment, ratchet gear 116 moves forward by turning clockwise to dispense medicament. As shown in FIG. 15B, in one embodiment, ratchet gear 116 includes a ratchet gear marker 1168. In one embodiment, alignment of ratchet gear marker 1168 with a protrusion 1030 on either of housing parts 1020*a* or 1020*b* prior to a first use of injection device 100 ensures that dosage mechanism 126 is in a proper pre-fired orientation. In one embodiment, protrusion 1030 prevents ratchet gear 116 from turning backwards by only allowing ratchet teeth 1164 to ramp over housing protrusion 1030.

Figure 7:
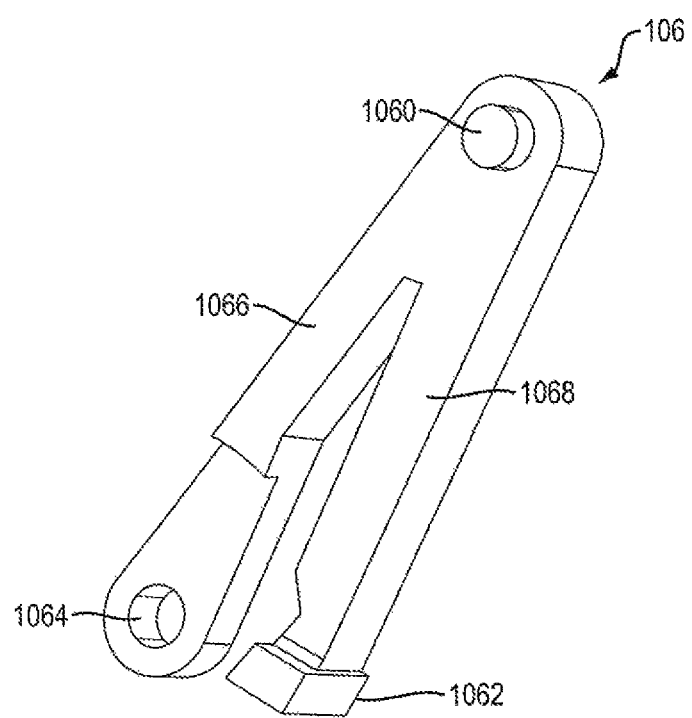
FIG. 7 is a perspective view of a ratchet arm of the injection device shown in FIG. 1A.
Figure 21:
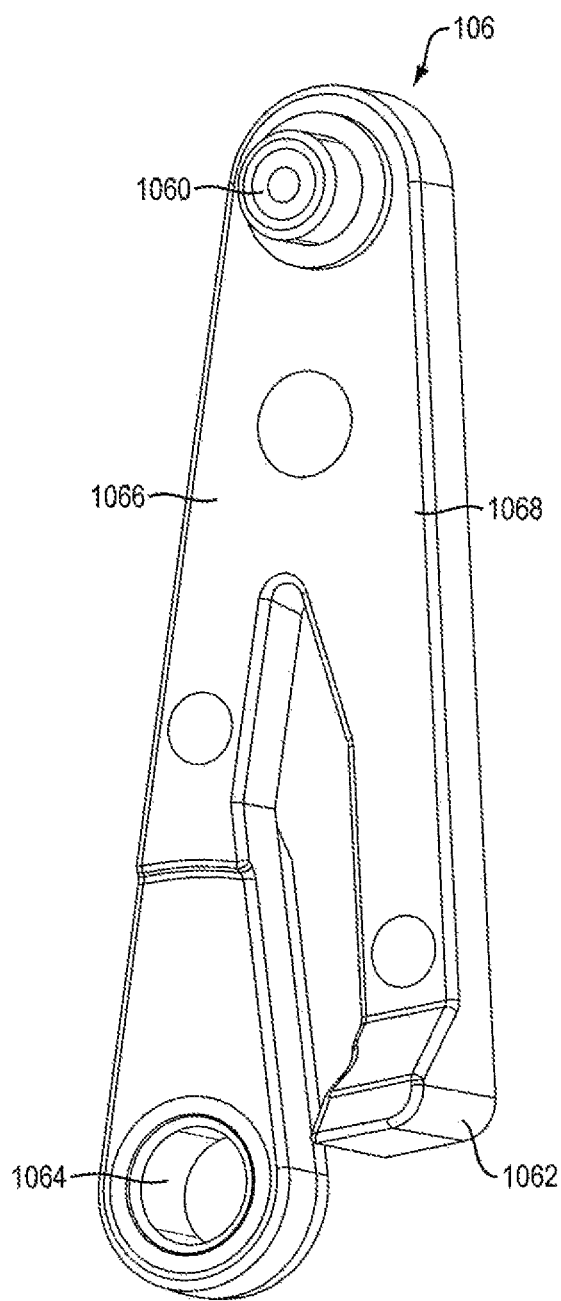
FIG. 21 is a perspective view of a ratchet arm of the injection device shown in FIG. 1D.

Referring to FIGS. 3A, 3B, 7, 17A, 17B, and 21, in one embodiment, the dosage mechanism 126 includes a crank arm 106. In one embodiment, as shown in FIGS. 7 and 21, crank arm 106 is generally V-shaped, having two legs, a crank arm leg 1066 and a pawl arm leg 1068. In one embodiment, crank arm leg 1066 includes a crank arm pivot hole 1064 at distal end which is configured to be slideably engageable with housing engagement member 1166*a* of the ratchet gear 116, which allows the crank arm 106 to be rotatable about axis 1160 but be axially fixed. In one embodiment, the crank arm pivot hole 1064 is generally aligned with axis 1160. In one embodiment, pawl arm leg 1068 includes a pawl tooth 1062 which is shaped to mesh with ratchet teeth 1164. In one embodiment, crank arm 106 includes a push button engagement member 1060, e.g., a projection, at the apex of crank arm 106 that extends from the apex towards slot 1046*b* on push button 104. In one embodiment, push button engagement member 1060 is configured to be slideably engageable with slot 1064*b*. In one embodiment, axially distal movement of push button 104 relative to housing 102 causes crank arm 106 to rotate about axis 1160 and pawl tooth 1062 to engage ratchet gear teeth 1164, causing ratchet gear 116 to rotate pinion teeth 1162 about axis 1160 that causes ram 108 to distally advance. In one embodiment, axially proximal movement of push button 104 relative to the housing 102 causes crank arm 106 to rotate about axis 1160 in an opposite direction and pawl tooth 1062 to disengage ratchet gear teeth 1164.

Figure 8:
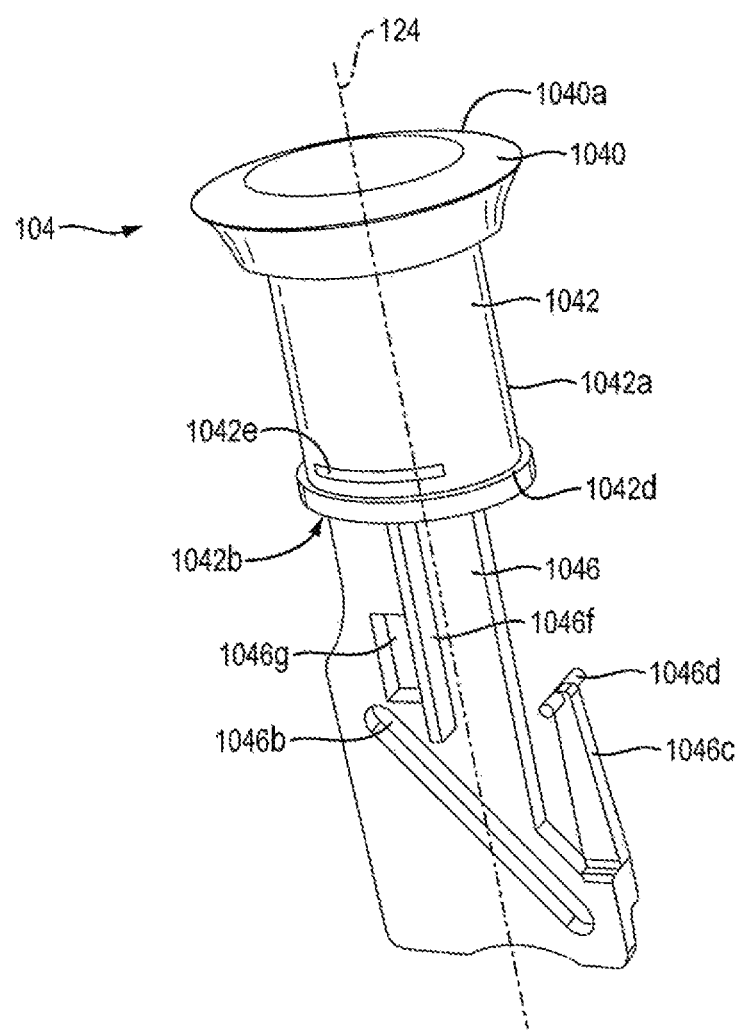
FIG. 8 is a perspective view of a first exemplary user-manipulable push button of the injection device shown in FIG. 1A.

With continued reference to FIGS. 3A, 3B, 17A and 17B, in one embodiment, the dosage mechanism 126 includes a user-manipulable push button 104 that allows the user to actuate the injection device 100. In one embodiment, as shown in FIG. 8, push button 104 is a unitary structure. In one embodiment, as shown in FIGS. 9A, 9B, and 9C, push button 104 is a non-unitary structure. In one embodiment, as shown in FIGS. 9A, 9B and 9C, push button 104 includes a cap 1040, a connector 1042, a force limiting biasing member 1044, and a base member 1046. In one embodiment, cap 1040 includes a user-contacting portion 1040a and tabs 1040b. In one embodiment, user-contacting portion 1040a has a hollow portion configured to facilitate connection with connector 1042. In one embodiment, tabs 1040b are configured to snap fit with corresponding features of connector 1042. In one embodiment, cap 1040 is molded from plastic. In other embodiments, cap 1040a is covered with a soft touch material. In one embodiment, tabs 1040b are sized and shaped to be fixed within connector 1042. In one embodiment, cap 1040 and connector 1042 are different colors. In one embodiment, when injection device 100 is in the fired state, connector 1042 is not visible. In one embodiment, when injection device 100 is not in a fired state, the connector 1042 is visible. In one embodiment, cap 1040 and connector 1042 are different colors so that a user can visually determine whether injection device 100 is in a fired state or not in a fired state.

Referring to FIGS. 9A, 9B and 9C, in one embodiment, connector 1042 of push button 104 includes connector body 1042a having a hollow portion 1042b, tabs 1042c, and a linear travel guide 1042f. In another embodiment, connector 1042 of push button 104 includes connector body 1042a having an indicating band 1042e. In one embodiment, tabs 1042c proximally extend from connector body 1042a. In another embodiment, tabs 1042c are sized and shaped to facilitate a fixed connection between cap 1040 and connector 1042. Cap 1040 and connector 1042 are shown as being fixedly connected via the use of tabs in FIG. 8. In other embodiments, cap 1040 and connector 1042 are integrally formed, such as by being made of a one-piece plastic injection molding, or a one-piece metal part.

In another embodiment, a linear travel guide 1042f extends from a distal portion of the connector body 1042a. In one embodiment, linear travel guide 1042f is configured to limit withdrawal of the push button from housing 102 and insertion of the push button into housing 102. In one embodiment, linear travel guide 1042f includes a shelf 1042d configured to engage housing 102 to limit withdrawal of the push button from housing 102. In one embodiment, linear travel guide 1042f includes a guide base 1042g configured to engage housing 102 to limit insertion of the push button into housing 102. In one embodiment, shelf 1042d is sized and shaped to engage with lip 1032 of housing 102 to limit withdrawal of the push button 104 from housing 102. In other embodiments, guide base 1042g is sized and shaped to engage a base engaging member 1034 of housing 102 to limit insertion of the push button 104 into the housing. In other embodiments, the linear travel guide 1042f is sized and shaped to slideably fit within shelf engaging openings 1036 of housing 102 to limit both the withdrawal and insertion of push button 104 into and out of housing 102. In one embodiment, linear travel guide 1042f is used to keep connector body 1042 aligned axially with the housing parts 1020a and 1020b. As shown FIG. 8, in some embodiments, the linear travel guide 1042f extends continuously along the circumference of the connector body 1042a. As shown in FIGS. 9A, 9B, and 9C, in other embodiments, linear travel guide 1042f extends discontinuously along the circumference of the connector body 1042a. In one embodiment, indicating band 1042e is configured to be visible to a user when push button 104 has been properly withdrawn from the housing 102 to prepare injection device 100 for medicament delivery. As shown in FIG. 8, in one embodiment, indicating band 1042e extends continuously along the circumference of connector body 1042a. As shown in FIGS. 9A, 9B, and 9C, in other embodiments, indicating band 1042e extends discontinuously along the circumference of connector body 1042a. In one embodiment, indicating band 1042e can incorporate a color, e.g., red, to add to the affect thereof. In one embodiment, when indicating band 1042e is visible, injection device 100 is in the ready (or reset) state. In one embodiment, when injecting band 1042e is not visible, injection device 100 is in the fired state. In one embodiment, hollow portion 1042b of connector body 1042a is sized and shaped to hold force limiting biasing member 1044.

Figure 10C:
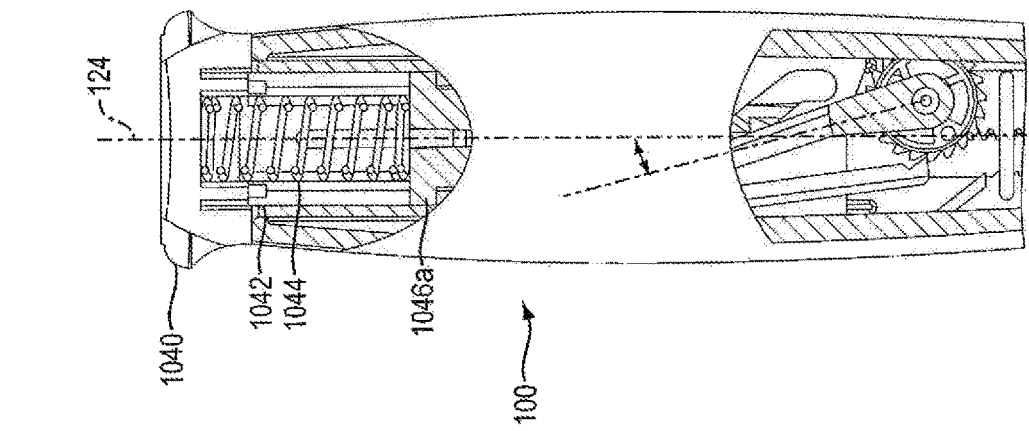
FIGS. 10A, 10B, and 10C are partial side cutaway views of the injection device shown in FIG. 1D during operation.
Figure 10B:
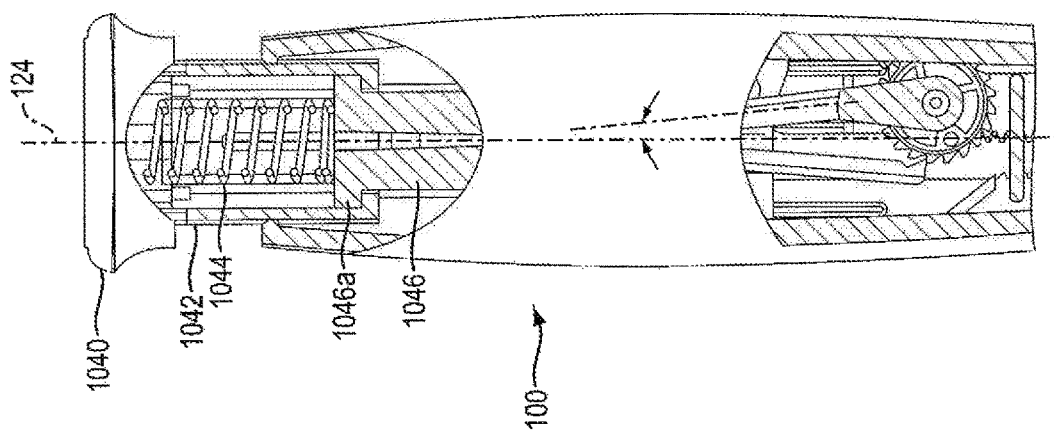
Figure 10A:
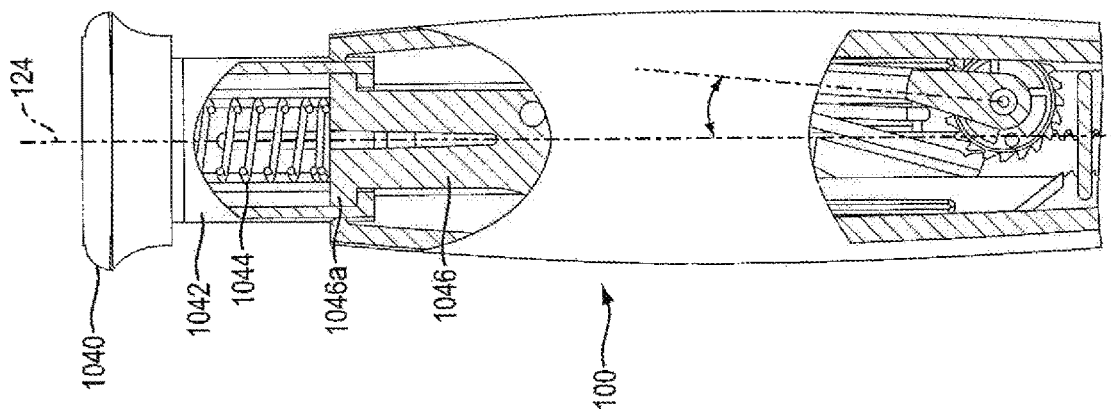

In one embodiment, force limiting biasing member 1044 of push button 104 is a metal, helically-coiled compression spring. In one embodiment, force limiting biasing member 1044 is disposed within hollow portion 1042b of connector body 1042a. In one embodiment, force limiting biasing member 1044 is captured in a pre-stressed force state between the interior end of cap 1040 and a top portion of flanges 1046a of base member 1046 (described in more detail below). In one embodiment, the pre-stressing force is at minimum as large as forces users exert on the push button during proper operation of injection device 100. In one embodiment, the pre-stressing force is no larger than what the dosing mechanism 126 can withstand without damage to the interacting components. Thus, in one embodiment, during normal actuation of injection device 100, force limiting biasing member 1044 does not further compress, as shown in FIGS. 10A, 10B, and 10C. FIGS. 10A, 10B, and 10C show an exemplary force limiting biasing member 1044 during normal operation of injection device 100. In another embodiment, as shown in FIGS. 11A, 11B, 11C, and 11D, force limiting biasing member 1044 is designed with sufficient spacing in its coiling, and with proper elastic properties, such that the force limiting biasing member 1044, by compression, can accommodate movement of push button 104 from a ready (or reset) state to a fired stated without movement of ram 108, ratchet gear 116, or crank arm 106, whereby force limiting biasing member 1044 can absorb actuation forces that could damage components. FIGS. 11A, 11B, 11C, and 11D show an exemplary force limiting biasing member 1044 compressing within connector 1042 which can occur when for example there a needle is miscoupled or occluded.

Referring to FIGS. 12A-12E, in one embodiment, injection device 100 has a ready (or reset) state wherein push button 104 is withdrawn from the housing 102 and indicator 1042 is visible to the user, as shown in FIG. 12C. In another embodiment, injection device 100 has a fired state wherein push button 104 is actuated and the base rim of cap 1040 is flush against a top portion of the housing 102, as shown in FIGS. 12A and 12E. In one embodiment, movement of push button 104 distally along axis 124 from a ready (or reset) state towards a fired state is considered firing motion, as shown in FIGS. 12C through 12E. Whereas, in another embodiment, movement of push button 104 proximally along axis 124 from a fired state towards a ready (or reset) state is considered resetting motion, as shown in FIGS. 12A through 12C.

Referring to FIG. 8, in one embodiment, base member 1046 includes a lockout aperture 1046g configured for use with a lock-out feature (described in more detail below). In one embodiment, base member 1046 of push button 104 includes flanges 1046a that are configured to be slideably connected within the hollow portion 1042b of connector 1042. In one embodiment, flanges 1046a are configured to be slideably connected to tracks disposed within the hollow portion 1042b of connector 1042 to ensure axial alignment of base member 1046 and connector 1042. In certain embodiments, the connection of flanges 1046a and the hollow portion 1042b of connector 1042 are such that base member 1046 is restricted to sliding generally axially along the interior surface of the hollow portion 1042 and such that the base member 1046 is restricted from generally rotating about the interior surface of the hollow portion 1042. In one embodiment, base member 1046 and housing 1020b are integrally connected to restrict movement of push button 104 to linear movements along axis 124. In certain embodiments, base member 1046 is configured to engage housing 102 to restrict movement of push button 104 to linear movement along axis 124. In certain embodiments, as shown in FIGS. 16B and 17B, base member 1046 has housing engagement slots 1046e that engage base member engagement plates 1021 of housing 1020b to restrict movement of push button 104 to linear movement along axis 124. As shown in FIG. 8, in another embodiment, base member 1046 has a housing engagement protrusion 1046f that is configured to engage base member engagement slot 1038 of housing 1020b to restrict movement of push button 104 to linear movements along axis 124.

Referring to FIG. 3B, in one embodiment, base member 1046 includes a slot 1046b disposed through the base member 1046. In one embodiment, slot 1046b is configured to engage push button engagement member 1060 of crank arm 106. In one embodiment, slot 1046b is slideably engageable with push button engagement member 1060. In one embodiment, slot 1046b is generally rectangular shaped. In another embodiment, slot 1046b is generally rectangular shaped with curved ends. In another embodiment, slot 1046b is generally polygonal. in another embodiment, slot 1046 is curved. In one embodiment, slot 1046b is oriented at an oblique angle with respect to axis 124. In one embodiment, translation of push button 104 distally or proximally along axis 124 causes push button engagement member 1060 to translate along the path of slot 1046b. In one embodiment, translation of push button 104 from a ready (or reset) state distally along axis 124 causes push button engagement member 1060 to translate along the path of slot 1046b, causing crank arm 106 to rotate about axis 1160. The path traced by slot 1046b could be of any geometry that crank arm engagement member 1060 could travel in. While keeping the start position and end position of this slot the same, a fixed dose can be achieved while varying the button force profile exerted by the user.

Referring to FIG. 9A, in one embodiment, slot 1046b of base member 1046 has portion 1046i and portion 1046j. In one embodiment, portion 1046i and portion 1046j of slot 1046b are at different angles with respect to axis 124. In one embodiment, portion 1046i is oriented at an oblique angle with respect to axis 124. In another embodiment, portion 1046j is oriented parallel to axis 124. In one embodiment, slot portion 1046j allows a user to translate push button 104 from a ready (or reset) state distally along axis 124 for a distance without movement of any other components of dosing mechanism 126. In one embodiment, translation of push button 104 distally along axis 124 from a ready (or reset) state translates push button engagement member 1060 (FIG. 7) along the path of slot portion 1046j, which keeps crank arm 106 from rotating about axis 1160 (FIG. 3B). In one embodiment, when push button engagement member 1060 is positioned at the most distal portion of slot portion 1046i, further translation of push button 104 distally along axis 124 translates push button engagement member 1060 along the path of slot 1046i, causing crank arm 106 to rotate about axis 1160. In one embodiment, the orientation of slot portion 1046j allows a user to press push button 104 for a period of time without injecting any medicament. In another embodiment, slot portion 1046i could have the same orientation with the same effect that push button 104 is pushed without the injection of medicament. The slot portion 1046j allows the user to build up momentum of push button 104 prior to injection of a medicament dose. Injection of medicament into a user can often time cause discomfort to the user, which can cause the user to withdraw the injection needle prior to full medicament dose injection. In one embodiment, the momentum of push button 104 that is built up as the user presses push button without injection of medicament is sufficient to allow for injection of a medicament dose with sufficient speed as to not provide the user time to react to any discomfort from medicament injection and withdraw the injection needle prior to full medicament dose injection. In another embodiment, the geometry of 1046j would have a vertical portion on the proximal end. In other embodiments, slot angles with longer or shorter sections alike 1046j or curved or parabolic slot would have changing force profiles of the button. In one embodiment a straight linear slot is implemented to keep constant force and contact with crank arm engagement member. In one embodiment, with a linear slot, the angle produced by the slot is a product of two dimensions. The vertical dimension, which stretches from the distal portion of the slot to the proximal portion of the slot and parallel to proximal-distal axis 124, is correlated to the desired button stroke. The horizontal dimension, perpendicular to proximal-distal axis 124 and stretching from the two furthest points on the slot directly correlate to the rotation of the crank arm 106.

Figure 1C:
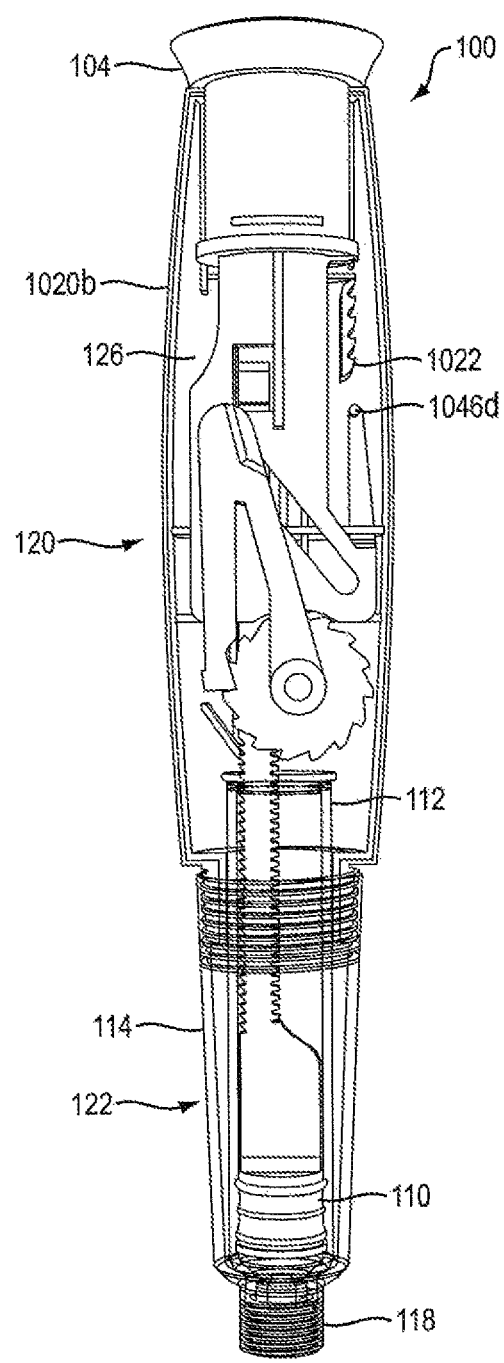
FIG. 1C is a cross-sectional front side view of the injection device shown in FIG. 1A.

In one embodiment, base member 1046 includes a flexible column 1046c extending proximally from a distal portion of base member 1046. In other embodiments, a column tooth 1046d extends perpendicularly from a proximal portion of flexible column 1046c. In certain embodiments, column tooth 1046d is generally almond shaped, as shown in FIG. 9A. In other embodiments, column tooth 1046d is generally cylindrically shaped, as shown in FIG. 8. In other embodiments, column tooth 1046d is generally polyhedronally shaped. Other shapes of column teeth 1046d are within the scope of this invention. In one embodiment, as shown in FIGS. 1B and 1C, column tooth 1046d is configured to engage the anti-retrograde ratchet side 1022b of unidirectional rack 1022. In one embodiment, a unidirectional rack 1022 is integrally formed on the internal surfaces of housing parts 1020a and 1020b. In one configuration, column tooth 1046d can be found in a double shear type load, which is known to be stronger and more stable than single shear configurations. In another embodiment, unidirectional rack 1022 is formed on the internal surface of only of housing parts 1020a and 1020b, placing unidirectional rack 1022 and column tooth 1046d in a single shear configuration.

In one embodiment, unidirectional rack 1022 has a smooth linear ratchet side 1022a and an anti-retrograde ratchet side 1022b. In one embodiment, the anti-retrograde ratcheted side 1022b of unidirectional rack 1022 is configured to engage column tooth 1046d and only allow movement of push button 104 in one direction, e.g., from the fired state to the ready (or reset) state. In certain embodiments, the anti-retrograde ratchet side 1022b of unidirectional rack 1022 has curved surfaces at both a proximal end and a distal end. In one embodiment, the proximal curved surface of anti-retrograde ratchet side 1022b is configured to bias the flexible column in a way to force column tooth 1046d to the smooth linear ratchet side 1022a of the unidirectional rack 1022. In one embodiment, the distal curved surface of anti-retrograde ratchet side 1022b is configured to bias the flexible column 1046c in a way to force column tooth 1046d to the anti-retrograde ratchet side 1022b of unidirectional rack 1022. In one embodiment, during resetting motion of push button 104, protrusions 1046d engage the distal curved surfaces of unidirectional rack 1022 causing flexible column 1046 to bias and forcing protrusions 1046d to the anti-retrograde ratchet side 1022b of unidirectional rack 1022, as shown in FIGS. 12A and 12B. In certain embodiments, if push button 104 is moved in a distal direction prior to completion of the resetting motion, protrusions 1046d would engage the ratchets of anti-retrograde ratchet side 1022b of unidirectional rack 1022, preventing distal movement. In one embodiment, during firing motion of push button 104, protrusions 1046d engage the proximal curved surfaces of anti-retrograde ratchet side 1022b of unidirectional rack 1022, causing flexible column 1046 to bias and forcing column tooth 1046d to the smooth linear ratchet side 1022a of unidirectional rack 1022, as shown in FIGS. 12C and 12D. In certain embodiments, the column tooth 1046d slides along the smooth linear ratchet side 1022a of unidirectional rack 1022 until the device is in the fired state. In one embodiment, the full amount of medicament which is to be expelled during the firing motion is only fully expelled upon push button 104 reaching the fired state. In one embodiment, if the push button does not complete the firing motion, the full amount of medicament for that dose is not fully expelled. In certain embodiments, a successive dose cannot be effectuated until the previous dosage amount of medicament is fully expelled. In one embodiment, the combination of the flexible column 1046c, column tooth 1046d and anti-retrograde ratchet side 1022b of unidirectional rack 1022 are considered the anti-reverse feature. In another embodiment, the combination of the interactions between the flexible column 1046c, column tooth 1046d and anti-retrograde ratchet side 1022b of unidirectional rack 1022, and the engagement of pawl 1026 of the housing 1020b with pawl engaging teeth 1082 are considered the anti-reverse feature.

Referring to FIG. 1C, in certain embodiments, the dosing mechanism 126 includes a lock-out feature, e.g., prevention of push button 104 from resetting from its fired position upon completion of the allotted medicament doses. In one embodiment, as shown in FIGS. 3A and 3B, the lock-out feature includes a protrusion 1094, which extends from a proximal portion of ram shaft 1086 in an opposite direction of support bar 1088 (FIG. 4), and a lockout aperture 1046g disposed in the base member 1046 of push button 104 (FIG. 8). In one embodiment, lockout aperture 1046g is disposed above slot 1046b. In one embodiment, protrusion 1094 is sized and shaped to protrude into lockout aperture 1046g. In one embodiment, lockout aperture 1046g is of a complimentary shape of protrusion 1094. In one embodiment, after each firing of the injection device 100, ram 108 is translated distally relative to the housing. In one embodiment, ram 108 is prevented from moving proximally relative to the housing because of engagement of pawl 1026 of the housing with pawl engaging teeth 1082. In one embodiment, after the final dose of medicament is expelled from the injection device, ram shaft 1086 is sufficiently distally translated so that when push button 104 reaches the fired state, protrusion 1094 and lockout aperture 1046g are aligned. In one embodiment, protrusion 1094 slides into lockout aperture 1046g thereby restricting movement of push button 104, e.g., push button 104 cannot reset because it is connected to ram shaft 1086 which is prevented from moving proximally relative to the housing by pawl 1026. In one embodiment, the proximal surface of protrusion 1094 is designed to promote protrusion 1094 sliding into lock out aperture 1046g. In one embodiment, the distal surface of protrusion 1094 is designed to remain engaged with the proximal surface of lockout aperture 1046g.

Referring to FIGS. 13A and 13B, in another embodiment, the lock-out feature includes a protrusion 1096 (as shown in FIG. 18), which extends from a proximal portion of ram shaft 1086, a lock-out member 2000 integrally formed within housing part 1020b, and a flange 1046h extending from base member 1046 towards housing 1020b. In one embodiment, lock-out member 2000 is only attached to the housing via a housing cross plate at a distal end of the lock-out member 2000. In one embodiment, lock-out member 2000 is flexible. In one embodiment, lock-out member 2000 includes a lockout deflector 2000a and a hook 2000b. In one embodiment, lockout deflector 2000a of lock-out member 2000 is centrally positioned on the lock-out member 2000. In one embodiment, lockout deflector 2000a of lock-out member 2000 is configured to engage protrusion 1096 of ram 108. In one embodiment, lockout deflector 2000a of lockout member 2000 is configured to slidingly engage protrusion 1096 of ram 108. In one embodiment, hook 2000b of lock-out member 2000 is positioned at a proximal end of lock-out member 2000. In another embodiment, hook 2000b is configured to engage flange 1046h of base member 1046. As shown in FIGS. 13A and 13B, in one embodiment, during the firing motion of push button 104 of the final medicament dose of the injection device 100, protrusion 1096 of ram 108 engages lockout deflector 2000a of lock-out member 2000. In one embodiment, engagement of protrusion 1096 and lockout deflector 2000a biases lock-out member 2000 such that hook 2000b extends into the path of flange 1046h. As shown in FIGS. 13C and 13D, in one embodiment, once hook extends into the path of flange 1046h, any attempted resetting motion of push button 104 would cause engagement of hook 2000b and flange 1046h. In one embodiment, engagement of hook 2000b and flange 1046h prevent any resetting motion of push button 104, thus, locking out the device from further use. In one embodiment, a portion of housing part 1020b is cut out in the shape of lock-out member 2000. The cut out portion of housing part 1020b is aligned with lock-out member 2000 so as to give a visual indication that the lock-out feature has been activated. In one embodiment, injection device 100 includes a cover 130 engagable with housing 102 that removably covers the cut out portion of housing part 1020b.

While the dosing mechanism described herein is shown as a part of a needled injection device for a liquid medicament, it is understood that the mechanism can be used in other dispensing devices that include a dispenser that is actuated by linear motion. This includes injection devices that use a mechanism other than a push button as well as other dispensing devices for gels or the like which may or may not contain a medicament.

In one embodiment, the dose size can be varied by changing the diameter of cartridge 112. In certain embodiments, a higher diameter will increase the dose size. In other embodiments, a smaller diameter will decrease the dose size. In one embodiment, varying the space between pawl engaging teeth 1082 and, correspondingly, pinion teeth 1162, can vary the dose size. In other embodiments, varying the shape of crank arm 106, the length of the crank arm leg 1066 or pawl arm leg 1068, or the angle of slot 1046b of base member 1046 can vary the dose size by varying the rotational angle of ratchet gear 116 caused by crank arm 106. These factors can be adjusted to derive an injector that contains a desired amount of liquid medicament and will produce the desired number of doses at a desired amount, and in certain embodiments fixed amount, and will have the desired dosing and resetting motions.

Each and every reference identified herein is incorporated by reference in its entirety. The entire disclosure of U.S. patent application publication number 2010/0036320 is hereby incorporated herein by reference thereto as if fully set forth herein. The term "about," as used herein, should generally be understood to refer to both the corresponding number and a range of numbers. Moreover, all numerical ranges herein should be understood to include each whole integer within the range.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The invention claimed is:

1. A dispensing mechanism, comprising:
a housing having a proximal-distal axis;
a ram within the housing, movable in a distal direction relative to the housing;
a push button moveable along the proximal-distal axis relative to the housing, the push button including a push button slot at a distal portion of the push button;
a crank arm having a pawl tooth, a pivot point, and a crank arm engagement member slideably engageable with the push button slot such that movement of the push button causes the crank arm engagement member to move along the push button slot, causing rotation of the crank arm about the pivot point; and
a ratchet gear having a first set of teeth releasably engageable with the pawl tooth and a second set of teeth releasably engageable with the ram,
wherein engagement of the pawl tooth with the first set of teeth of the ratchet gear causes the ratchet gear to rotate, causing the ram to distally advance relative to the housing, and
wherein the ram includes a lockout protrusion and the push button includes a lockout aperture, the lockout aperture engaging with the lockout protrusion in a locked position.

2. The dispensing mechanism of claim 1, further comprising an anti-reverse mechanism including:
at least one housing ratchet integrally formed on an internal surface of the housing; and
a flexible column integrally formed extending from a distal portion of the push button, the flexible column having a flexible column protrusion at a proximal end thereof,
wherein as the push button moves along the proximal-distal axis, the flexible column protrusion engages the housing ratchet and restricts movement of the push button to one direction during a resetting motion.

3. The dispensing mechanism of claim 2, wherein the flexible column protrusion is almond shaped.

4. The dispensing mechanism of claim 1, wherein the ram includes at least two sets of teeth.

5. The dispensing mechanism of claim 4, wherein at least one set of teeth has involute spur rack geometry.

6. The dispensing mechanism of claim 4, wherein a first set of ram teeth are configured to engage the second set of teeth of the ratchet gear, and a second set of ram teeth are configured to engage a housing protrusion, the housing protrusion being integrally formed within the housing and configured to facilitate movement of the ram in one direction.

7. The dispensing mechanism of claim 6, wherein the first set of ram teeth and the second set of teeth of the ratchet gear have similar corresponding involute gear teeth geometry.

8. The dispensing mechanism of claim 1, wherein the push button slot is oriented at an oblique angle with respect to the proximal-distal axis.

9. The dispensing mechanism of claim 1, wherein the push button slot has a portion that is oriented at an oblique angle with respect to the proximal-distal axis and a portion that is oriented parallel to the proximal-distal axis.

10. The dispensing mechanism of claim 1, wherein the first set of teeth of the ratchet gear control a dose amount of an injector.

11. An injector comprising:
the dispensing mechanism of claim 1;
a cartridge disposed within the housing;
a medicament contained within the cartridge;
a plunger disposed in the cartridge to seal the medicament therein, wherein the ram is associated with the plunger for forcing the plunger in a distal direction relative to the housing for ejecting a dose of the medicament; and
a needle in fluid communication with the cartridge for injecting doses of the medicament into a patient.

12. The injector of claim 11, wherein the medicament includes a parathyroid hormone.

13. The injector of claim 12, wherein the parathyroid hormone is teriparatide.

14. The injector of claim 11, wherein the medicament includes glucagon-like peptide receptor agonists.

15. The injector of claim 14, wherein the glucagon-like peptide receptor agonists are exenatide.

16. The injector of claim 14, wherein the glucagon-like peptide receptor agonists are liraglutide.

17. The dispensing mechanism of claim 1, wherein the lockout protrusion engages with the lockout aperture in the locked position after a dose of a medicament is ejected.

18. The dispensing mechanism of claim 1, wherein the lockout protrusion engages a sidewall of the lockout aperture to restrict movement of the push button when the lockout protrusion is in the locked position.

19. The dispensing mechanism of claim 18, wherein the lockout protrusion prevents proximal movement of the push button relative to the housing when the lockout protrusion is in the locked position.

20. The dispensing mechanism of claim 1, wherein the dispensing mechanism is configured to eject a plurality of doses of a medicament including a final dose of the medicament and the lockout protrusion engages the lockout aperture in the locked position after the final dose of the medicament is ejected.

21. The dispensing mechanism of claim 1, wherein the ram is prevented from moving proximally relative to the housing in the locked position.

* * * * *